(12) United States Patent
Nishikawa et al.

(10) Patent No.: US 6,811,833 B2
(45) Date of Patent: Nov. 2, 2004

(54) 4-MEMBERED RING COMPOUND AND OPTICAL PHASE OPTICAL RETARDATION PLATE USING THE SAME

(75) Inventors: Naoyuki Nishikawa, Kanagawa (JP); Kentaro Toyooka, Kanagawa (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 138 days.

(21) Appl. No.: 10/244,404

(22) Filed: Sep. 17, 2002

(65) Prior Publication Data

US 2003/0102458 A1 Jun. 5, 2003

(30) Foreign Application Priority Data

Sep. 17, 2001 (JP) ........................................ 2001-281649
Aug. 2, 2002 (JP) ........................................ 2002-225638

(51) Int. Cl.[7] ..................... C09K 19/52; C07C 233/57; C07C 327/24; C07C 271/36; C07D 333/22
(52) U.S. Cl. ........................ 428/1.1; 549/72; 558/366; 558/433; 560/21; 560/25; 560/76; 564/152; 564/154; 564/155
(58) Field of Search ............... 252/299.01, 299.61, 252/299.63, 299.67; 428/1.1; 549/72; 558/366, 433; 560/21, 25, 76; 564/152, 154, 155

(56) References Cited

U.S. PATENT DOCUMENTS 5,198,583 A * 3/1993 Bisacchi et al. ............ 564/158

FOREIGN PATENT DOCUMENTS

| EP | 1118324 | * | 7/2001 |
| JP | 61-212532 A | | 9/1986 |
| JP | 10-68816 A | | 3/1998 |
| JP | 2000-284126 A | | 10/2000 |
| JP | 2001-4837 A | | 1/2001 |

OTHER PUBLICATIONS

EPO Search Report dated Nov. 26, 2002 in corresponding EP Application No. 02020559.7–1521.
Fusae Nakanishi et al, "Photoreactive Crystals: Photodimerization of a Diolefinic Derivative Accompanied by isomerization," *Mol. Cryst and Liq Cryst.*, May 2001, vol. 356, pp. 15–22.

\* cited by examiner

Primary Examiner—Shean C. Wu
(74) Attorney, Agent, or Firm—Burns, Doane, Swecker & Mathis, L.L.P.

(57) ABSTRACT

A 4-membered compound is represented by the following formula (I) is disclosed (in the formula, $X^1$ and $X^2$ each independently represent an oxygen atom, a sulfur atom or a substituted or unsubstituted imino group, $Y^1$ and $Y^2$ each independently represent a single bond, an oxygen atom or a substituted or unsubstituted imino group, $B^1$ and $B^2$ each independently represent an optionally substituted aliphatic, aliphatic carbonyl, aromatic or aromatic carbonyl group having 1-20 carbon atoms, and $A^1$ and $A^2$ each independently represent a group represented by the following formula (II) ($Ar^1$, $Ar^2$ and $Ar^3$ each independently represent a cyclic group having 5–14 carbon atoms, $L^1$ and $L^2$ each independently represent a single bond or a divalent linking group, and p represents an integer of 0–2)). There is also disclosed a birefringence medium containing a 4-membered compound represented by the formula (I) and an optical element comprising the birefringence medium.

Formula (I):

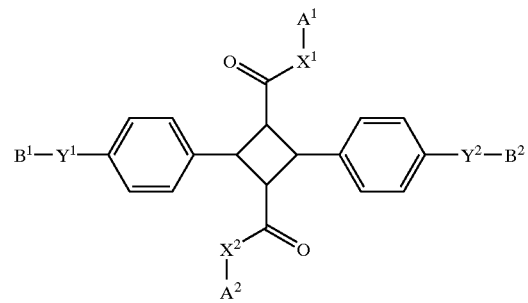

Formula (II):

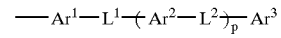

14 Claims, 3 Drawing Sheets

4-MEMBERED RING COMPOUND AND OPTICAL PHASE OPTICAL RETARDATION PLATE USING THE SAME

TECHNICAL FIELD

The present invention relates to novel 4-membered ring compounds which are useful in producing optical elements. The present invention also relates birefringence medium s and optical elements utilizing the 4-member ring compounds, such as optical phase retardation plates and films and displays having its films, elliptically polarizing plates, circularly polarizing plates, polarization rotation plate, polarization conversion prism, optical pick up devices, reflective liquid crystal devices, semi-transmissive liquid crystal devices, transmissive liquid crystal devices, touch-sensitive panels, antireflection films, which may be used in optical analysis apparatuses, optical measurement apparatuses, apparatuses for optical experiments and so forth.

RELATED ART

As optical retardation plates, there are provided thin plates formed of an inorganic material such as calcite, mica and quartz crystal and oriented polymer films having a high intrinsic birefringence characteristic. Examples of practical use of such an optical retardation plate include a quarter-wavelength plate (henceforth abbreviated as "¼λ plate"), which converts a linearly polarized light into a circularly polarized light, and a half-wavelength plate (henceforth abbreviates as "½λ plate"), which changes a polarization vibration plane of a linearly polarized light by 90°. As for a monochromatic light, these optical retardation plates can give an optical phase difference corresponding to ¼λ or ½λ of the wavelength of the light. However, as for a white light that is a composite light of lights in the visible region, they show dispersion of polarization states for various wavelengths, and thus they convert a white light into a colored polarized light. This is due to the wavelength-dependent property in phase difference shown by a material constituting the optical retardation plates In order to solve such a problem, there have been studied various wide band optical retardation plates that can provide uniform phase difference for lights of a wide wavelength region (for example visible region).

For example, Japanese Patent Laid-open Publication (Kokai, henceforth referred to as JP-A) No. 10-68816 discloses an optical retardation plate comprising a quarter-wavelength plate showing a phase difference of quarter-wavelength for birefringence light and a half-wavelength plate showing a phase difference of half-wavelength for birefringence light, which are bonded so that their optical axes should cross each other. Further, JP-A-10-90521 discloses an optical retardation plate of a structure that at least two of optical retardation plates having an optical phase difference value of 160–320 nm are laminated so that their slow axes should be neither parallel with nor perpendicular to each other or one another.

Furthermore, JP-A-11-52131 discloses a laminate type optical retardation plate showing a wavelength-dependent dispersion value a smaller than 1 and having a structure that Birefringence medium A and Birefringence medium B, at least one of which comprises a liquid crystal compound showing homogenous molecular orientation, are laminated so that their slow axes should orthogonally cross each other. This optical retardation plate satisfies a relationship of $\alpha_A < \alpha_B$ where $\alpha_A$ and $\alpha_B$ represent wavelength-dependent dispersion values $\alpha$ ($\alpha = \Delta n$ (450 nm)/$\Delta n$ (650 nm)) for birefringence factors $\Delta n$ of Birefringence medium A and Birefringence medium B, respectively, and a relationship of $R_A > R_B$ where $R_A$ and $R_B$ represent phase difference R of the birefringence media, respectively.

Moreover, JP-A-2000-284126 discloses an optical retardation plate in which an optically anisotropic layer showing a retardation value of 210–300 nm at a wavelength of 550 nm and an optically anisotropic layer showing such a value of 115–150 nm are laminated, one of the optically anisotropic layers consists of a polymer film and the other consists of a layer formed from liquid crystal molecules, and JP-A-2001-4837 discloses an optical retardation plate in which a first optically anisotropic layer comprising liquid crystal molecules and substantially showing a phase difference of $\pi$ and a second optically anisotropic layer comprising liquid crystal molecules and substantially showing a phase difference of $\pi/2$ are provided on a transparent support of long length, a slow axis in a plane of the first optically anisotropic layer and the longitudinal direction of the transparent support substantially forms an angle of 75°, and slow axes in planes of the first and second optically anisotropic layers substantially form an angle of 15°. It is explained that all the optical retardation plates disclosed in the aforementioned publications specifically consist of a laminate of two sheets of birefringence medium, and they can achieve λ/4 in a large wavelength region.

However, in the production of the optical retardation plates disclosed in JP-A-10-68816 and JP-A-10-90521, a complicated production process is required in order to control optical directions (optical axis or slow axis) of the two sheets of polymer films. Optical direction of a polymer film in the form of a sheet or rolled film generally corresponds to the longitudinal direction or transverse direction of the film. It is difficult to industrially produce a polymer film having an optical axis or slow axis along an oblique direction in a sheet or roll in a large scale. Moreover, in the optical retardation plates disclosed in JP-A-10-68816 and JP-A-10-90521, the optical directions of two polymer films must be adjusted so that they should neither parallel nor perpendicular to each other. Therefore, in order to produce these optical retardation plates, there are required steps of cutting two kinds of polymer films in predetermined angles and adhering the obtained chips. Since these steps are troublesome, through these steps, axes are likely to be misaligned, the production of quality and the yielding percentage are likely to lower, the cost of production is likely to increase and the deterioration of quality is likely to happen due to pollution. Further, it is also difficult to strictly regulate the optical phase difference value of a polymer film.

On the other hand, also in the optical retardation plates disclosed in JP-A-11-52131 and JP-A-2000-284126, two kinds of birefringence media must be laminated so that their slow axes should cross perpendicularly, although homogenously oriented liquid crystal compounds are used for at least one of the birefringence media. Further, the invention disclosed in JP-A-2001-4837 also requires control of angles of the layers, and thus requires a complicated production process.

Furthermore, a thinner optical retardation plate is required in recent years for use in reflected type liquid crystal displays, and improvement of laminate type optical retardation plates has been desired also in respect of film thickness.

SUMMARY OF THE INVENTION

The present invention has been accomplished in view of the aforementioned various problems, and its object is to provide a novel 4-membered ring compound useful for an optical retardation plate, in particular, a novel 4-membered ring compound that, when it is used in an optical retardation plate, corrects wavelength-dependent dispersion shown by a birefringence medium and imparts wavelength-dependent dispersion that provides uniform phase difference for lights within a certain wavelength region to the birefringence medium.

Another object of the present invention is to provide a birefringence medium that can provide uniform phase difference for lights within a certain wavelength region and can be easily manufactured, and various optical members using the same, such as optical phase retardation plates and films, elliptically polarizing plates, circularly polarizing plates, polarization rotaion plate, polarization conversion prism, optical pick up devices, reflective liquid crystal devices, semi-transmissive liquid crystal devices, transmissive liquid crystal devices, touch-sensitive panels, antireflection films and so forth.

According to an aspect of the present invention, there is provided a 4-membered ring compound represented by the following formula (I).

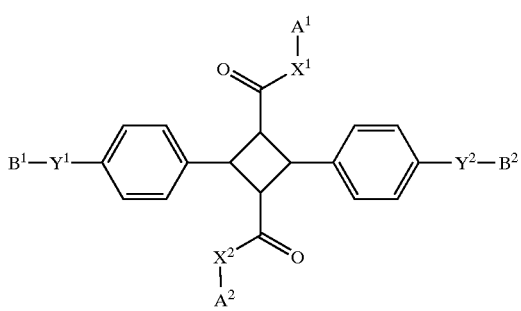

Formula (I)

In the formula, $X^1$ and $X^2$ each independently represent an oxygen atom, a sulfur atom or a substituted or unsubstituted imino group, $Y^1$ and $Y^2$ each independently represent a single bond, an oxygen atom or a substituted or unsubstituted imino group, and $B^1$ and $B^2$ each independently represent an optionally substituted aliphatic group, aliphatic carbonyl group, aromatic group or aromatic carbonyl group, having 1–20 carbon atoms. Two of the benzene rings directly bonding to the cyclobutane ring each may have a substituent on the rings. $A^1$ and $A^2$ each independently represent a group represented by the following formula (II):

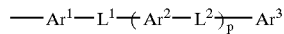

Formula (II)

In the formula, $Ar^1$, $Ar^2$ and $Ar^3$ each independently represent a cyclic group having 5–14 carbon atoms, which may have a substituent on the ring. $L^1$ and $L^2$ each independently represent a single bond or a divalent linking group. p represents an integer of 0–2, and when p is 2, two of $Ar^2$ and two of $L^2$ may be identical to or different from each other.

As preferred embodiments of the present invention, there are provided the aforementioned 4-membered ring compound, wherein rings of the cyclic groups represented by $Ar^1$, $Ar^2$ and $Ar^3$ are rings selected from a benzene ring, a thiophene ring and a naphthalene ring; the aforementioned 4-membered ring compound, wherein $L^1$ and $L^2$ each independently represent a single bond or a divalent linking group selected from an acetylene group, a bisacetylene group, a carbonyloxy group and an oxycarbonyl group; the aforementioned 4-membered ring compound, wherein $L^1$ and $L^2$ each independently represent an acetylene group or a bisacetylene group; the aforementioned 4-membered ring compound, wherein $Y^1$ and $Y^2$ each independently represent an oxygen atom or a substituted or unsubstituted imino group; the aforementioned 4-membered ring compound, wherein $B^1$ and $B^2$ each independently represent an aliphatic group or aliphatic carbonyl group substituted with a substituent containing a divalent group consisting of an oxygen atom, a sulfur atom, a carbonyl group, a substituted or unsubstituted imino group or a combination thereof; the aforementioned 4-membered ring compound, wherein $B^1$ and $B^2$ each independently represent an aliphatic group or aliphatic carbonyl group substituted with a substituent containing a polymerizable group; and the aforementioned 4-membered ring compound, wherein $B^1$ and $B^2$ each independently represent an aliphatic group or aliphatic carbonyl group substituted with an acryloyl group or a methacryloyl group.

According to another aspect of the present invention, there is provided a birefringence medium containing the aforementioned 4-membered ring compound.

As preferred embodiments of the present invention, there are provided the aforementioned birefringence medium comprising at least one kind of liquid crystal compound fixed in an oriented state; and aforementioned birefringence medium, wherein the content of the 4-membered compound is 0.5 to 50 weight %.

According to another aspect of the present invention, there is provided an optical element comprising aforementioned birefringence medium.

Incidentally, as compounds relating to the compound represented by the aforementioned formula (I), there are mentioned photodimerized hydroxycinnamic acid derivatives mentioned in J. Chem. Soc., Perkin Trans. 2, p.109 (1993) and so forth and substituted diphenyl group-containing cyclobutanedicarboxylic acid derivatives as pharmaceutically effective ingredients of analgesics discloses in JP-A-2001-199884. However, any of these references do not specifically mention the 4-membered ring compound of the present invention, and they do not specifically suggest the present invention.

DETAILED DESCRIPTION OF THE INVENTION

Figure 1:
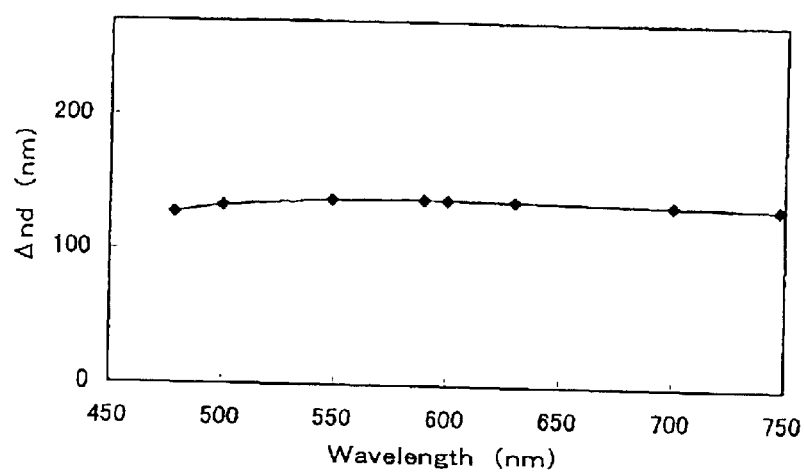
FIG. 1 shows a plot representing wavelength dependency of optical phase difference in a visible region for the optical retardation plate produced in Example 32.

First, the compound represented by the following formula (I) will be explained.

Formula (I)

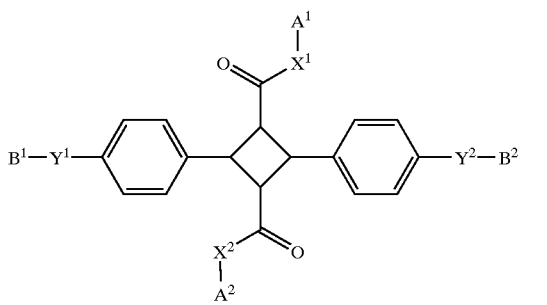

In the aforementioned formula (I), $X^1$ and $X^2$ each independently represent an oxygen atom, a sulfur atom or a substituted or unsubstituted imino group. They particularly preferably represent an oxygen atom or an imino (—NH—). Examples of the substituent of the imino group include a lower alkyl group (including straight, branched and cyclic alkyl groups, the same shall apply to any "alkyl group" mentioned hereinafter) and a lower alkanoyl group (including any alkanoyl groups containing a straight, branched or cyclic alkyl group, the same shall apply to any "alkanoyl group" mentioned hereinafter).

In the aforementioned formula (I), $Y^1$ and $Y^2$ each independently represent a single bond, an oxygen atom or a substituted or unsubstituted imino group. They particularly preferably represent a single bond, an oxygen atom or an imino (—NH—). Examples of the substituent of the imino group include a lower alkyl group and a lower alkanoyl group.

In the aforementioned formula (I), $B^1$ and $B^2$ each independently represent an aliphatic group, aliphatic carbonyl group, aromatic group or aromatic carbonyl group, having 1–20 carbon atoms, which may have a substituent. $B^1$ and $B^2$ are preferably an aliphatic group or an aliphatic carbonyl group.

The aliphatic group and aliphatic carbonyl group preferably have 4–18 carbon atoms, more preferably 8–12 carbon atoms. The aliphatic group contained in the aforementioned aliphatic group or aliphatic carbonyl group may be a straight, branched or cyclic aliphatic groups (the same shall apply to any "aliphatic group" mentioned hereinafter), and it include an alkyl group, an alkenyl group, an alkynyl group, a cycloalkyl group and so forth. The aliphatic group and the aliphatic carbonyl group may have a substituent. Examples of the substituent include substituents containing a divalent group consisting of an oxygen atom, a sulfur atom, a carbonyl group, a substituted or unsubstituted imino group or a combination thereof. More specifically, there can be mentioned substituents containing a divalent group such as oxygen atom (—O—), carbonylimino (—CONH—), iminocarbonyl (—NHCO—), oxycarbonyl (—OCO—) and carbonyloxy (—COO—).

The aromatic group and aromatic carbonyl group preferably have 6–20 carbon atoms, more preferably 10–18 carbon atoms. The aromatic group and the aromatic carbonyl group may have a substituent. Examples of the substituent include alkyl group and alkoxy groups.

Further $B^1$ and $B^2$ preferably have a substituent containing a polymerizable group. The polymerizable group mentioned herein include a crosslinkable group that crosslinks molecules. The aforementioned polymerizable group is preferably an acryloyl group or a methacryloyl group.

In the aforementioned formula (I), two of the benzene rings directly bonding to the cyclobutane ring may independently have a substituent. Examples of preferred substituents include an alkyl group having 1–6 carbon atoms, an alkoxy group having 1–6 carbon atoms (including alkoxy groups containing a straight, branched and cyclic alkyl group, the same shall apply to any "alkoxy group" mentioned hereinafter), an alkylthio group having 1–6 carbon atoms (including alkylthio groups containing a straight, branched or cyclic alkyl group, the same shall apply to any "alkylthio group" mentioned hereinafter) and a halogen atom. Specifically, there can be mentioned methyl, methoxy, methylthio, fluorine atom, chlorine atom, bromine atom and so forth.

In the aforementioned formula (I), $A^1$ and $A^2$ each independently represent a group represented by the following formula (II).

Formula (II)

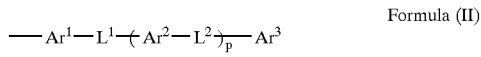

In the aforementioned formula (II), $Ar^1$, $Ar^2$, and $Ar^3$ each independently represent a cyclic group having 5–14 carbon atoms. The cyclic group is preferably a group derived from a 5-membered ring, 6-membered ring, 7-membered ring or condensed ring structure formed by these rings, more preferably a 5-membered ring, 6-membered ring or condensed ring structure formed by these rings. The ring of the aforementioned cyclic group may be an aromatic ring (including both of a carboaromatic ring and a heteroaromatic ring, the same shall apply to any "aromatic ring" mentioned hereinafter), an aliphatic ring or a heterocyclic ring. It is particularly preferably an aromatic ring, and specific examples thereof include benzene ring, thiophene ring, pyridine ring, pyrimidine ring, naphthalene ring, cyclohexane ring, piperidine ring, dioxane ring and so forth. Benzene ring, naphthalene ring and thiophene ring are particularly preferred. Further, $Ar^1$, $Ar^2$ and $Ar^3$ may have a substituent on the ring. As the substituent, preferred are an alkyl group having 1–6 carbon atoms, an alkoxy group having 1–6 carbon atoms, an alkylthio having 1–6 carbon atoms and a halogen atom. More specifically, preferred are methyl, methoxy, methylthio, fluorine atom, chlorine atom, bromine atom and so forth. Further, the substituents on the rings of $Ar^1$, $Ar^2$ and $Ar^3$ may bond to each other to form a ring.

In the aforementioned formula (II), $L^1$ and $L^2$ each independently represent a single bond or a divalent linking group. As the linking group, preferred are a divalent linking group consisting of an oxygen atom, sulfur atom, carbonyl, ethylene (—C=C—), acetylene (—C≡C—), a substituted or unsubstituted imino group or a combination thereof. Especially, a single bond, acetylene, bisacetylene (—C≡C—C≡C—), carbonyloxy (—COO—) and oxycarbonyl (—OCO—) are more preferred, and acetylene and bisacetylene are still more preferred. Examples of the substituent of the aforementioned imino group include a lower alkyl group and a lower alkanoyl group.

In the aforementioned formula (II), p represents an integer of 0–2. It is preferably 0 or 1, more preferably 0. In addition, when p is 2, two of $Ar^2$ or $L^2$ may be identical to or different from each other.

The compound represented by the aforementioned formula (I) may exist in the forms of two or more of stereoisomers depending on steric configurations of substituents on the cyclobutane ring, and all such stereoisomers fall within the scope of the present invention. It is particularly preferred that —CO—X$^1$-A$^1$ and —CO—X$^2$-A$^2$, which are the substituents at the 1-position and 3-position, should have different configurations, i.e., one should be in α-configuration and the other should be in β-configuration. Similarly, as for -Ph-Y$^1$—B$^1$ and -Ph-Y$^2$—B$^2$ (Ph is phenylene group), which are the substituents at the 2- and 4-positions, it is preferred that one should be in a-configuration and the other should be in β-configuration.

Particularly preferred examples of the compound of the present invention are mentioned below. However, the present invention is not limited to the following examples.

Compound 1

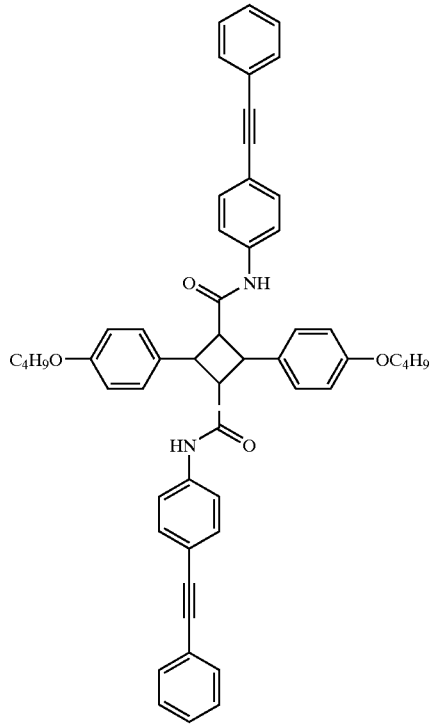

Compound 2

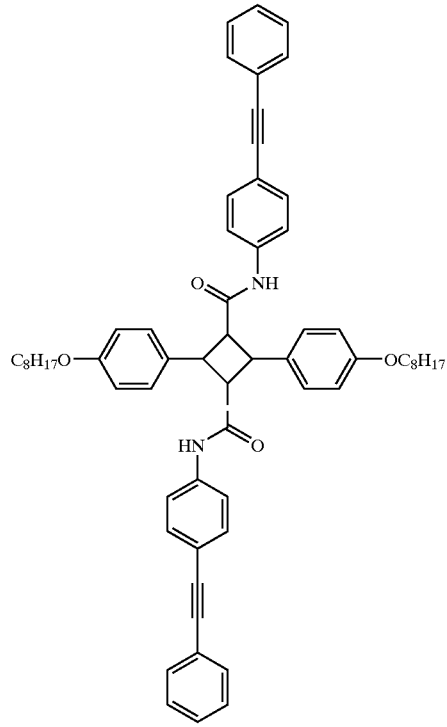

Compound 3

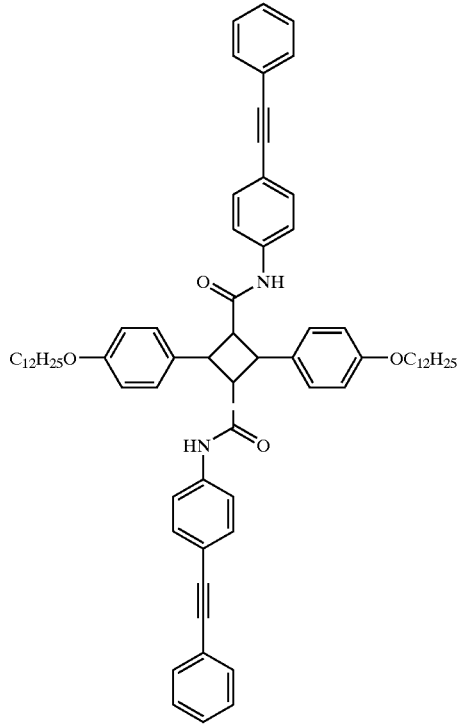

Compound 4

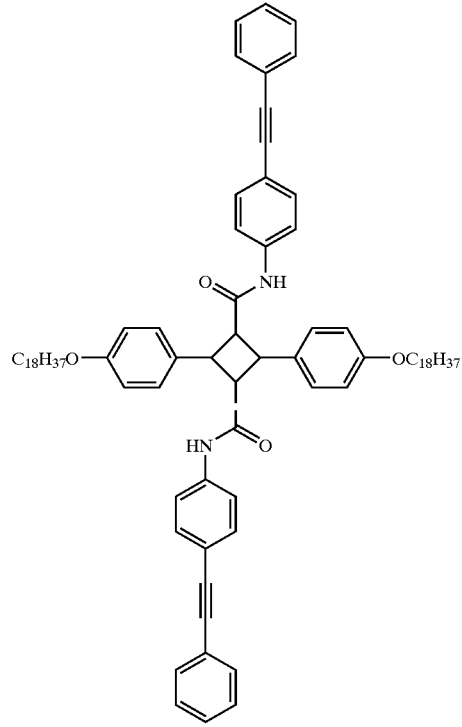

-continued
Compound 5
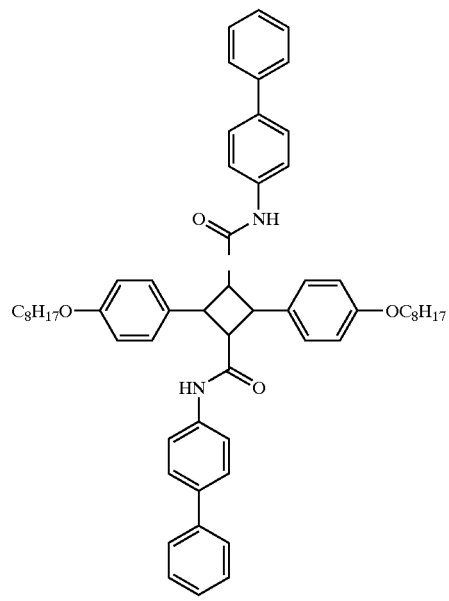
Compound 6
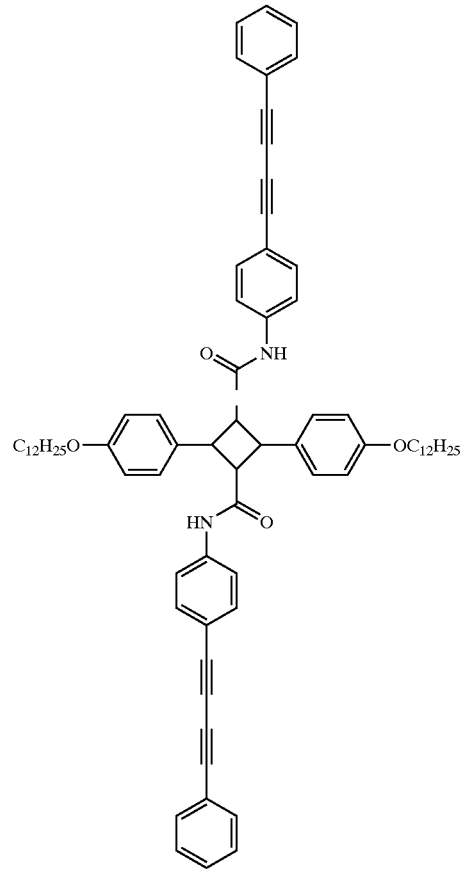
Compound 7
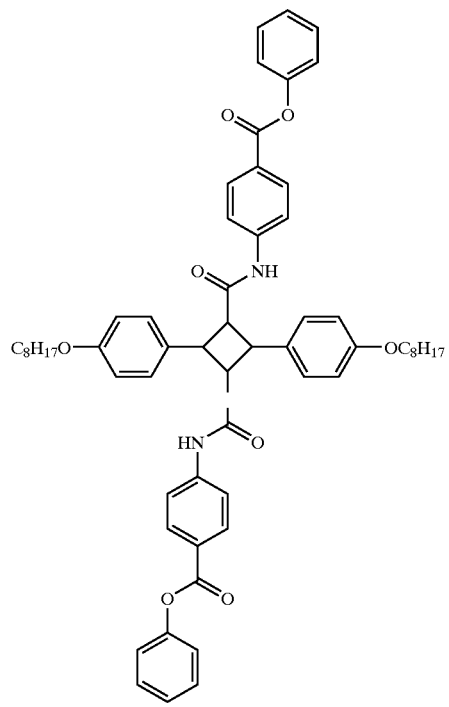
Compound 8
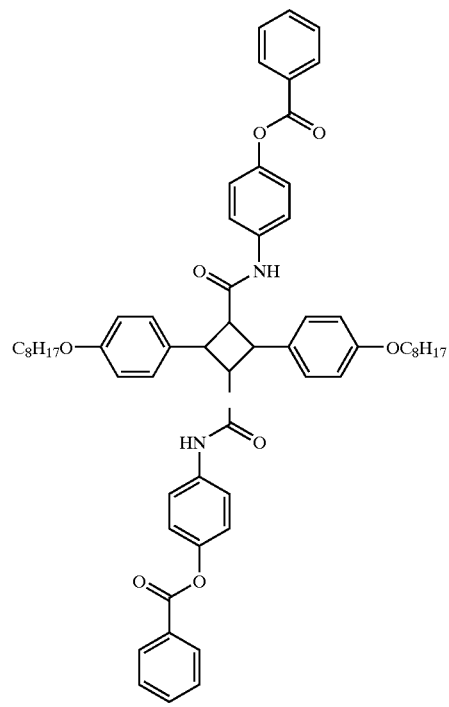

Compound 9
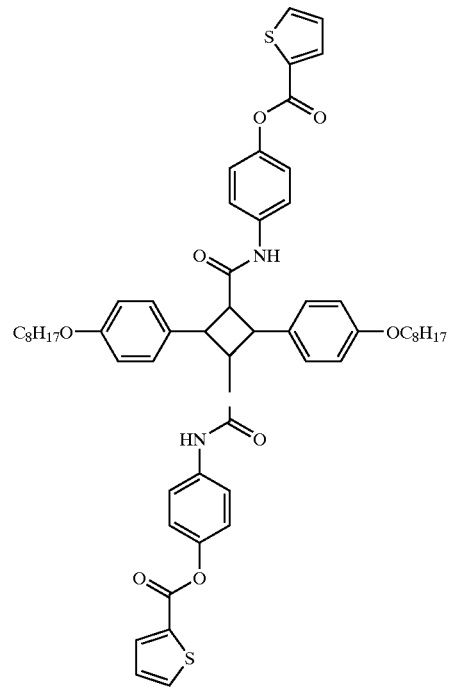
Compound 10
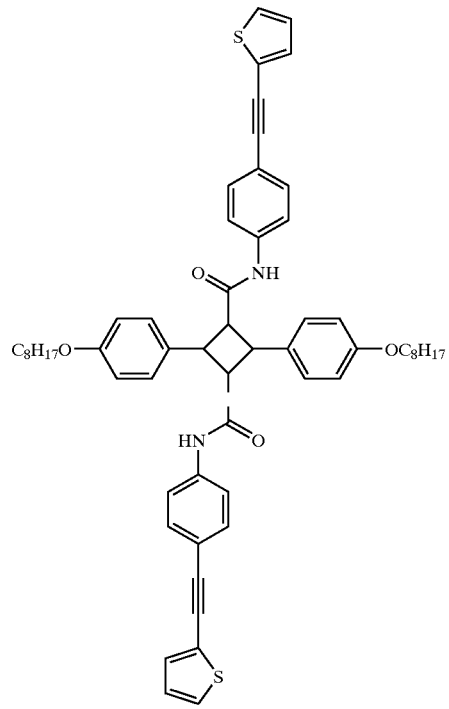
Compound 11
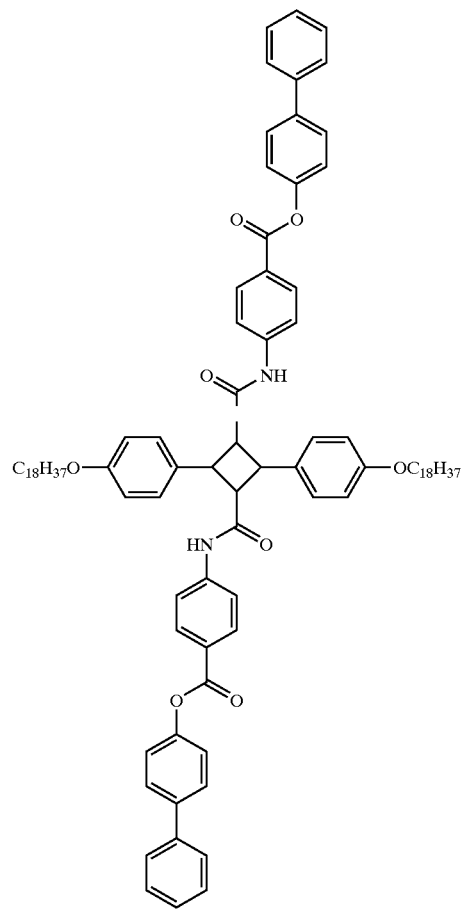
Compound 12
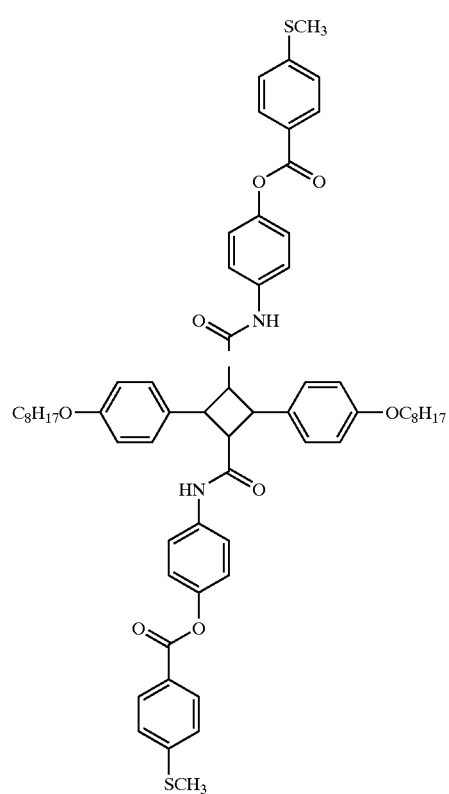

-continued
Compound 13
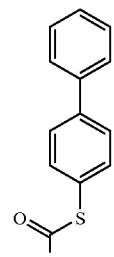
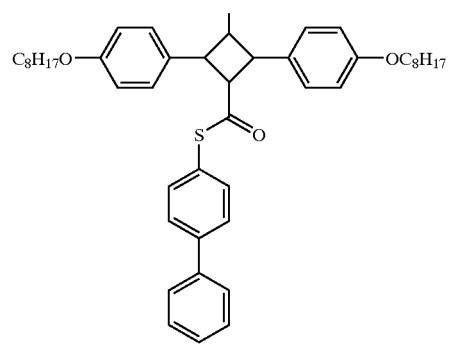
Compound 14
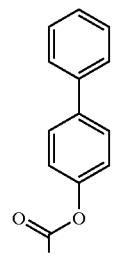
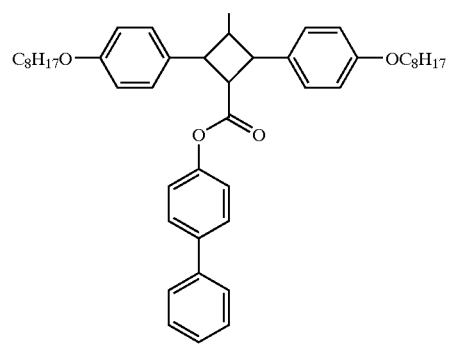
Compound 15
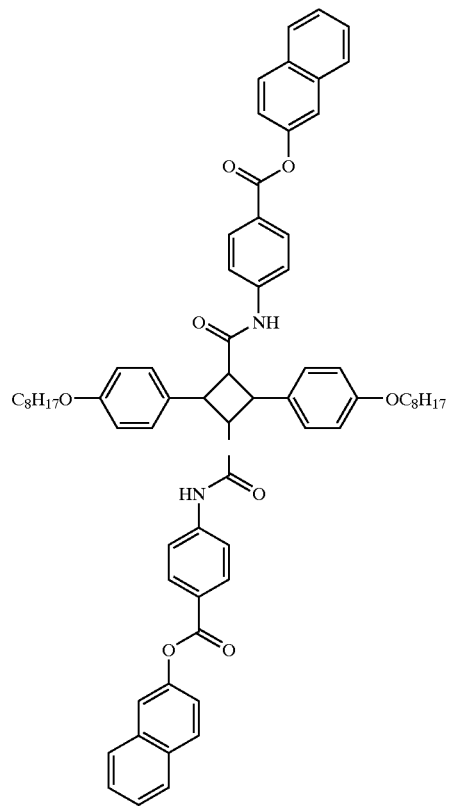
Compound 16
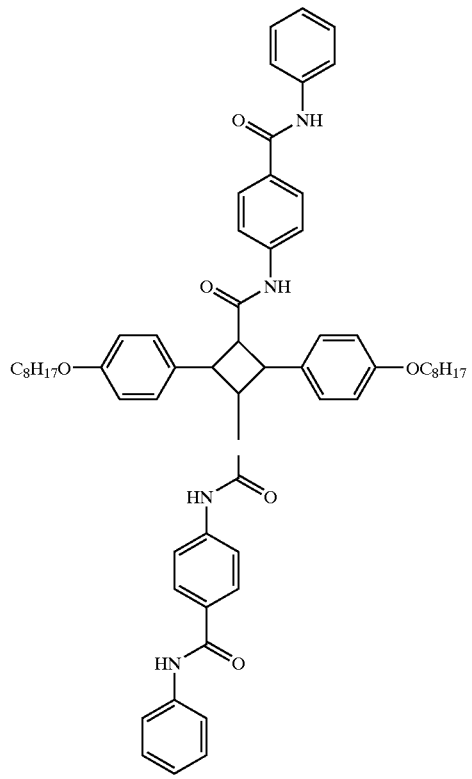

Compound 17
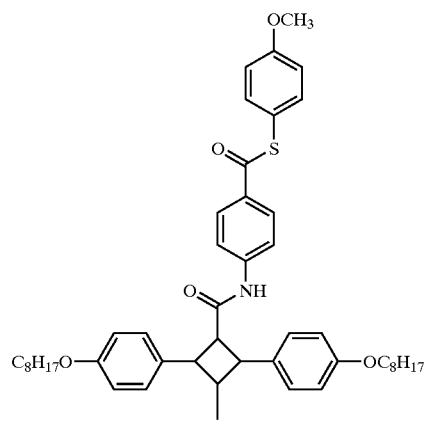
Compound 18
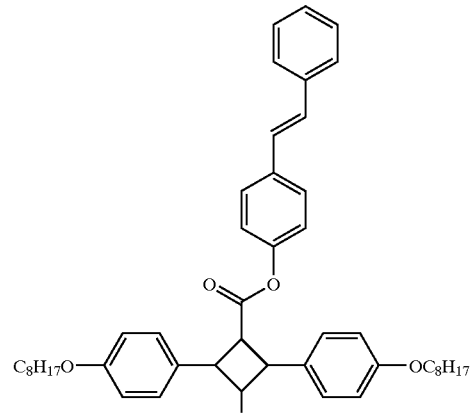
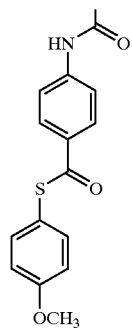
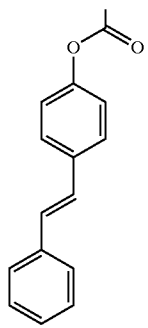
Compound 19
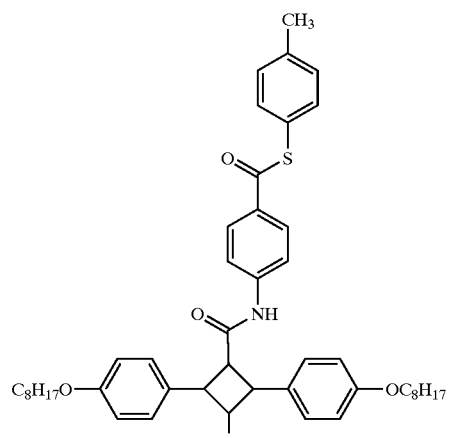
Compound 20
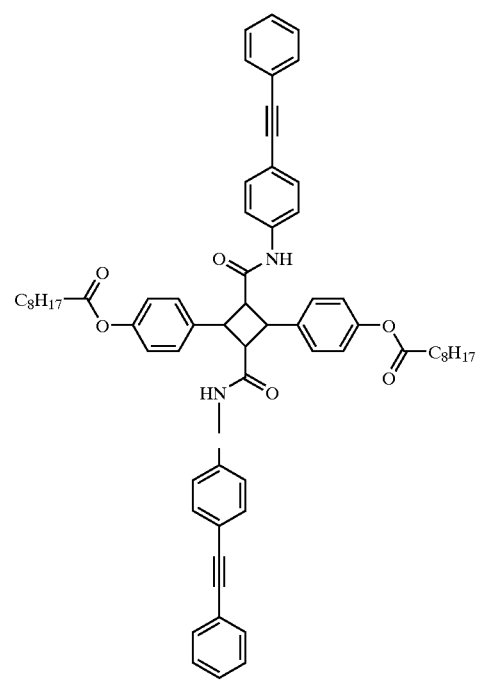
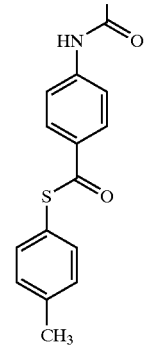

Compound 21
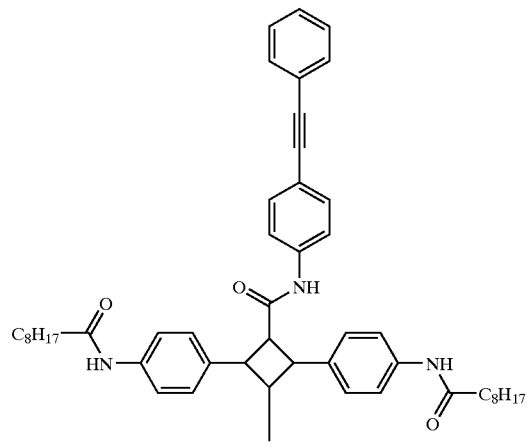
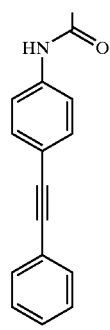
Compound 22
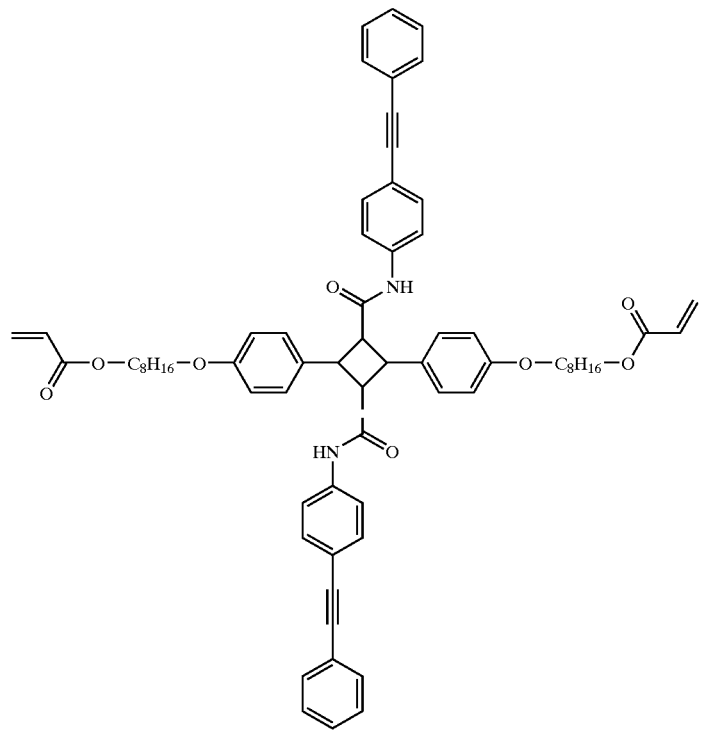

Compound 23
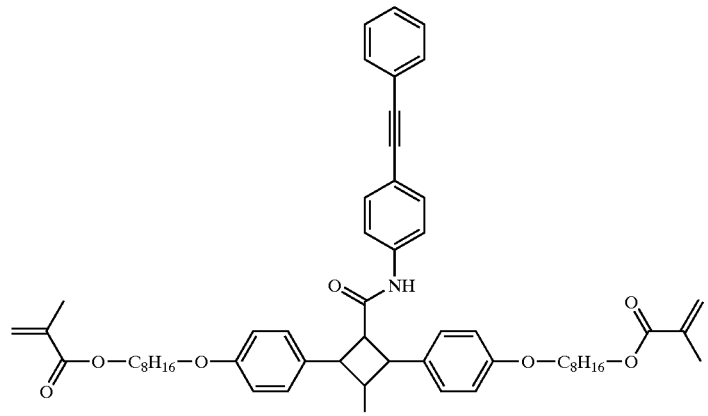
Compound 24
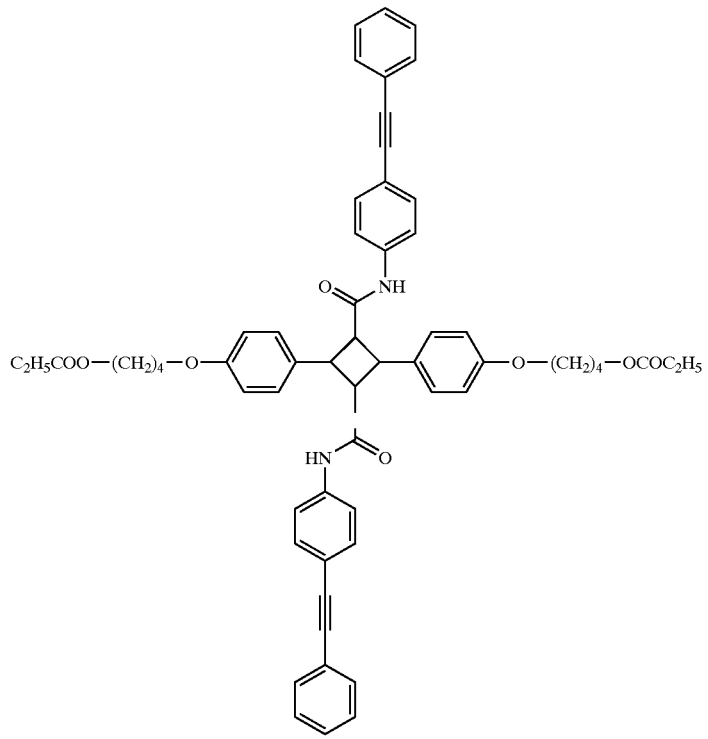

Compound 25
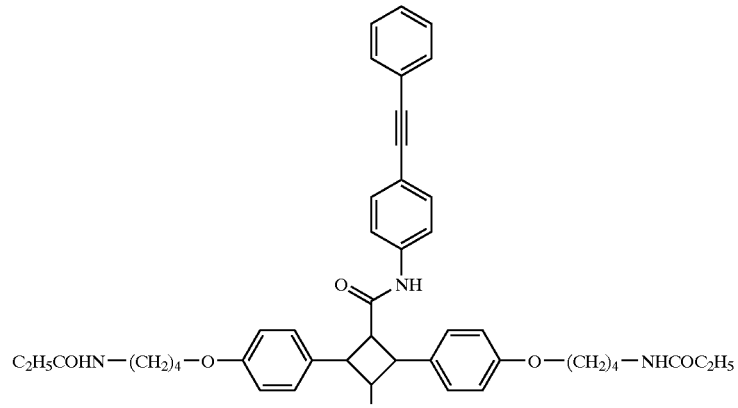
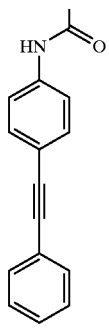
Compound 26
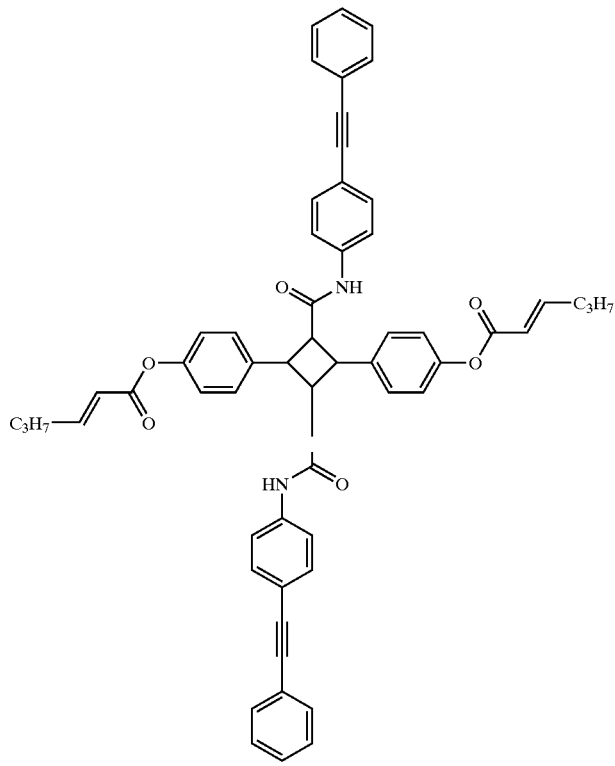

Compound 27
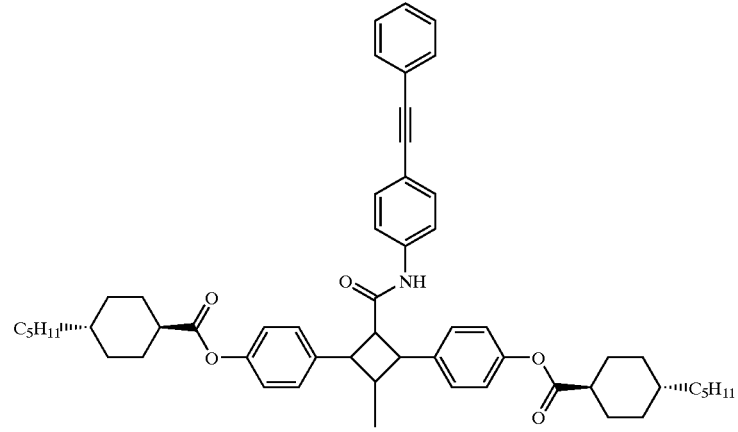
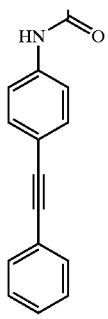
Compound 28
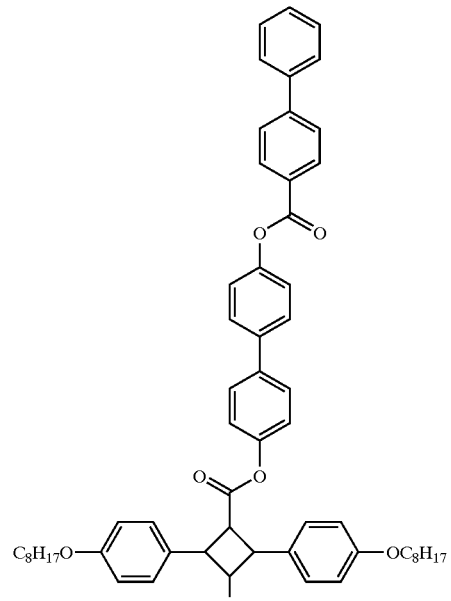

-continued
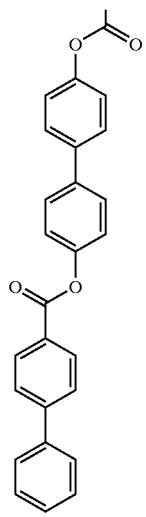
Compound 29
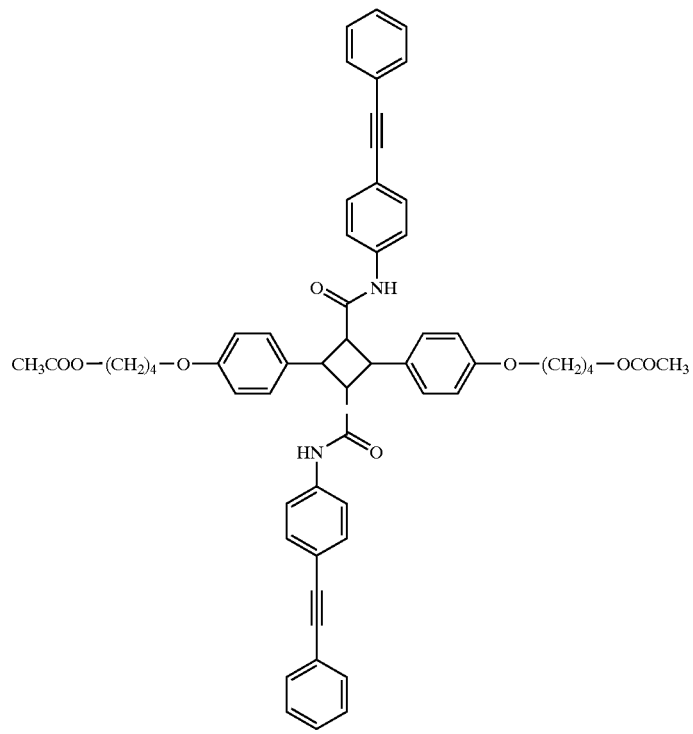
Compound 30
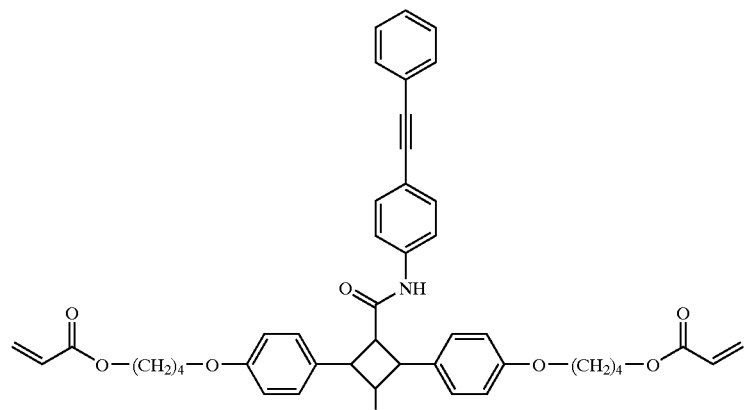

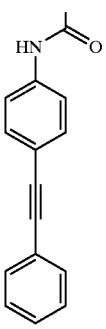
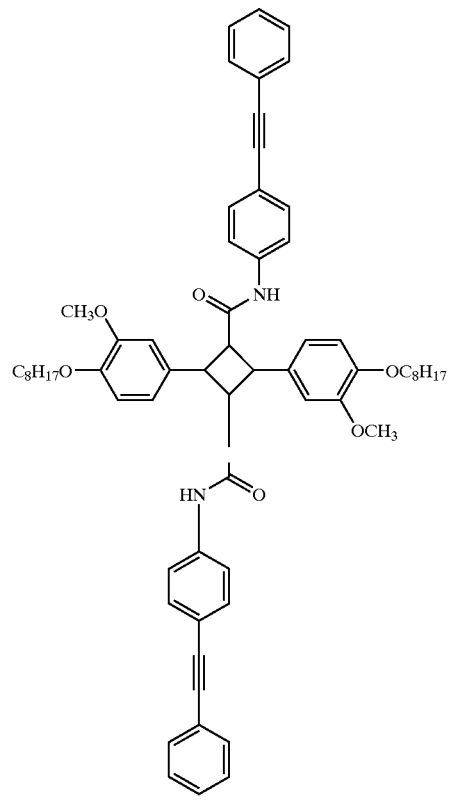
Compound 31
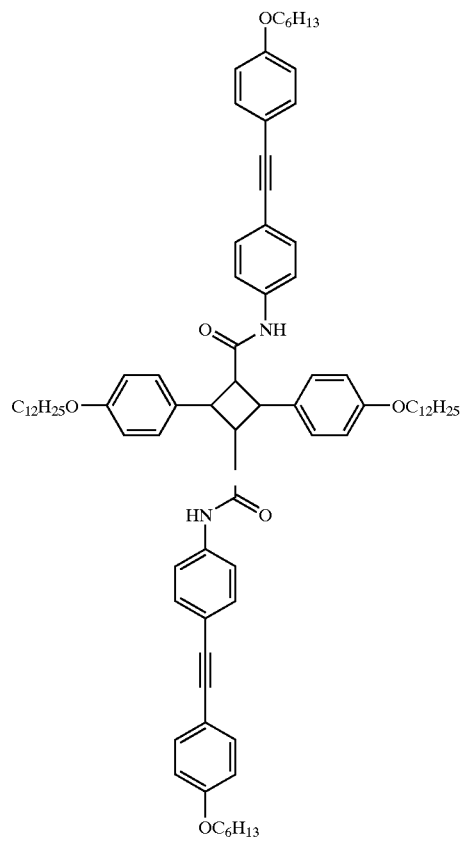
Compound 32
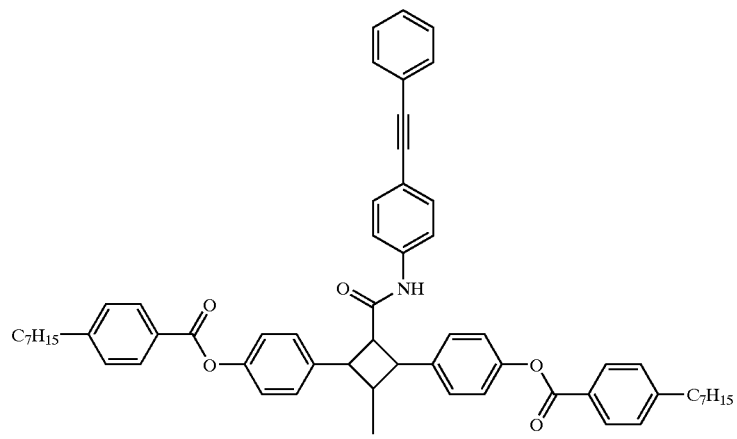
Compound 33

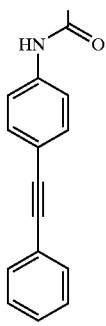
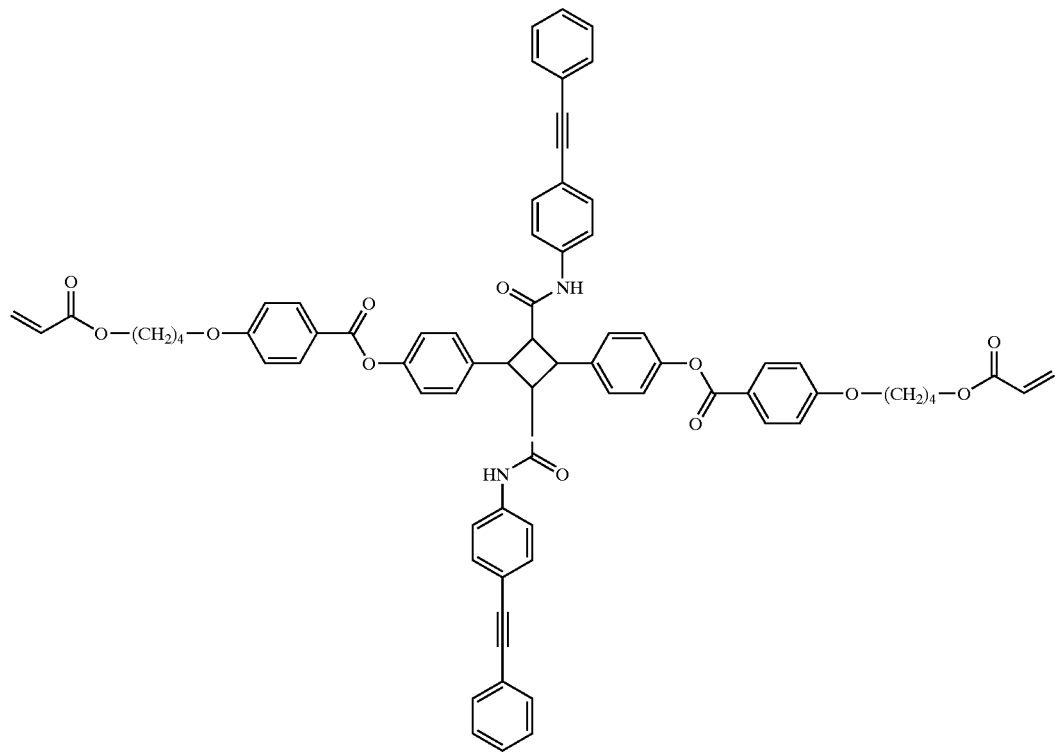
Compound 34
The compounds represented by the aforementioned formula (I) can be synthesized according to the methods shown in Schemes 1 to 4 mentioned below. However, the present invention is not limited to these methods.
Scheme 1
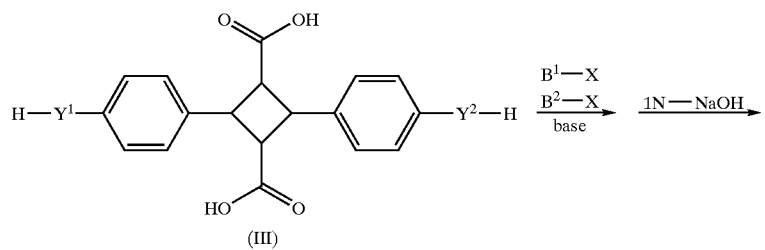

-continued

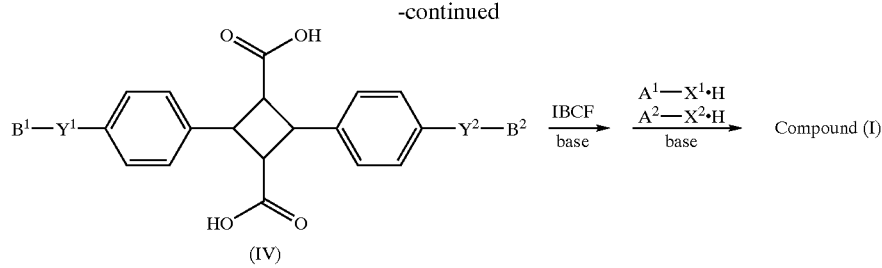

(IV)

In the formulas, $X^1$, $X^2$, $A^1$, $A^2$, $B^1$ and $B^2$ have the same meanings as defined above. $Y^1$ and $Y^2$ each represent —NH—, —NR— (R is an alkyl group, the same shall apply to the following descriptions), —O— or —S—, and X represents a leaving group. Further, in the scheme, IBCF represents isobutyl chloroformate, and Compound (I) represents a compound represented by the aforementioned formula (I).

In the method of Scheme 1, a compound represented by the formula (III) is used as a starting material, and it is allowed to react with compounds represented as $B^1$—X and $B^2$—X in the presence of a base. Examples of the leaving group X include a halogen atom, an alkylsulfonyloxy group and an arylsulfonyloxy group. The base used in this reaction may be either an inorganic base or an organic base. Preferred examples of the base include sodium carbonate, potassium carbonate, triethylamine, diisopropylethylamine and so forth. Then, a compound represented by the aforementioned formula (IV) can be obtained by hydrolysis. The compound represented by the aforementioned formula (IV) and compounds represented as $A^1$-$X^1$—H and $A^2$-$X^2$—H, respectively, can be condensed to obtain a target compound represented by the aforementioned formula (I). The base used in this reaction is preferably an organic base such as triethylamine and diisopropylethylamine. For the condensation of the compound represented by the aforementioned formula (IV) and the compounds represented as $A^1$-$X^1$—H and $A^2$-$X^2$—H, respectively, the mixed acid anhydride method can be preferably used. However, as other methods, there can also be preferably used methods utilizing, for example, dicyclohexylcarbodiimide (DCC), carbonyldiimidazole (CDI) or the like as a condensation agent.

Scheme 2

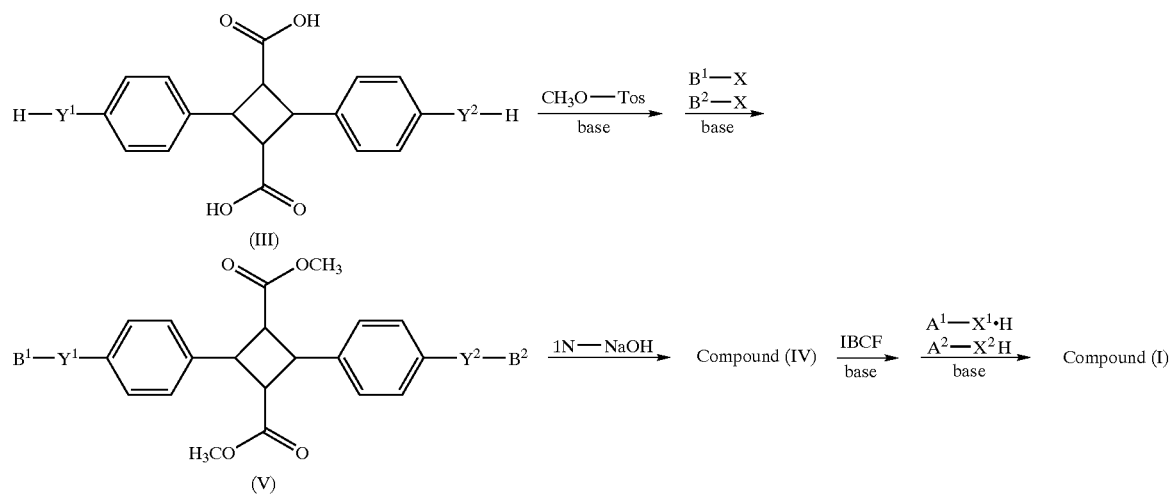

In the formulas, $X^1$, $X^2$, $A^1$, $A^2$, $B^1$ and $B^2$ have the same meanings as defined above. $Y^1$ and $Y^2$ each represent —NH—, —NR—, —O— or —S—, and X represents a leaving group. Further, in the scheme, IBCF represents isobutyl chloroformate, Compound (I) represents a compound represented by the aforementioned formula (I), and Compound (IV) represents a compound represented by the aforementioned formula (IV).

In the method of Scheme 2, a compound represented by the formula (III) and methyl paratoluenesulfonate are allowed to react in the presence of a base to form a dimethyl ester compound. The base used in this reaction is preferably an organic base such as triethylamine and diisopropylethylamine. Then, the dimethyl ester compound is allowed to react with compounds represented as $B^1$—X and $B^2$—X, respectively, in the presence of a base and thereby converted into a compound represented by the formula (V). The base used in this reaction may be either an inorganic base or an organic base. Preferred examples of the base include sodium carbonate, potassium carbonate, triethylamine, diisopropylethylamine and so forth. The compound represented by the aforementioned formula (V) can be converted into a compound represented by the formula (IV) by hydrolysis and thereafter subjected to a condensation reaction in the same manner as in Scheme 1 to obtain a target compound represented by the formula (I).

Scheme 3

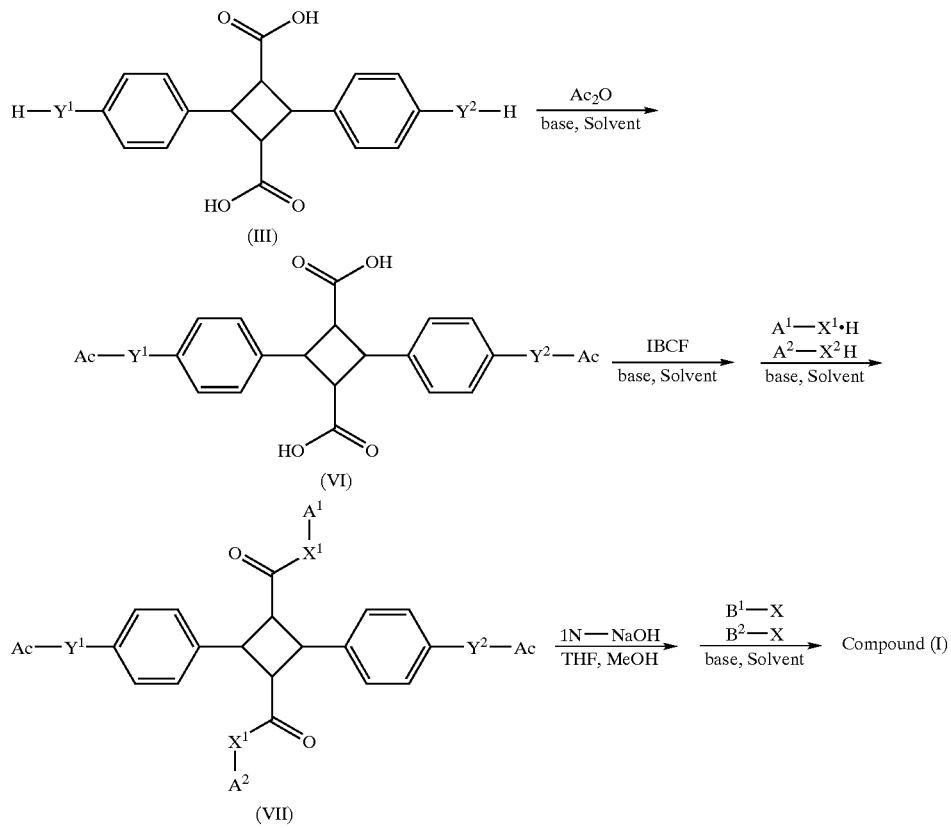

In the formulas, $A^1$, $A^2$, $B^1$ and $B^2$ have the same meanings as defined above. $X^1$ and $X^2$ each represent —NH— or —NR—, and $Y^1$ and $Y^2$ represent —O— or —S—. X represents a leaving group. In the scheme, Compound (I) represents a compound represented by the aforementioned formula (I).

In the method of Scheme 3, a compound represented by the formula (III) is allowed to react with acetic anhydride in the presence of a base and thereby converted into a compound represented by the formula (VI). The base used in this reaction is preferably an organic base such as triethylamine and diisopropylethylamine. In this step, a method of utilizing an acetyl halide instead of acetic anhydride can also be used. Then, the compound represented by the aforementioned formula (VI) is condensed with compounds represented as $A^1$-$X^1$—H and $A^2$-$X^2$—H, respectively, and thereby converted into a compound represented by the formula (VII). The base used in this reaction is preferably an organic base such as triethylamine and diisopropylethylamine. For the condensation of the compound represented by the aforementioned formula (VI) and the compounds represented as $A^1$-$X^1$—H and $A^2$-$X^2$—H, respectively, the mixed acid anhydride method can be preferably used. However, as other methods, there can also be preferably used methods utilizing, for example, dicyclohexylcarbodiimide (DCC), carbonyldiimidazole (CDI) or the like as a condensation agent. Finally, the compound represented by the formula (VI) can be hydrolyzed and then allowed to react with compounds represented as $B^1$—X and $B^2$—X, respectively, in the presence of a base to obtain a target compound represented by the formula (I). The base used in this reaction may be either an inorganic base or an organic base. Preferred examples of the base include sodium carbonate, potassium carbonate, triethylamine, diisopropylethylamine and so forth.

Scheme 4

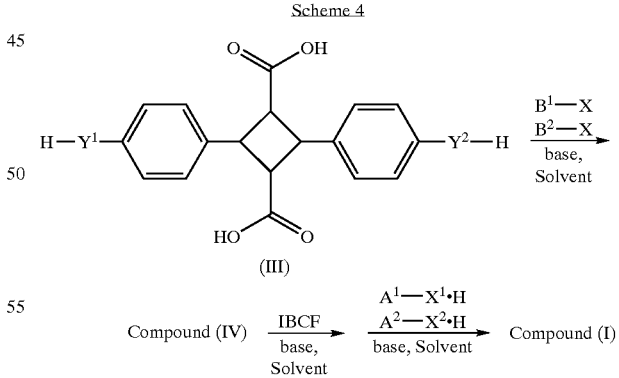

In the formulas, $A^1$, $A^2$, $B^1$ and $B^2$ have the same meanings as defined above. $X^1$ and $X^2$ each represent —NH— or —NR—, and $Y^1$ and $Y^2$ each represent —O— or —S—. X represents a leaving group. In the scheme, IBCF represents isobutyl chloroformate, Compound (I) represents a compound represented by the aforementioned formula (I), and Compound (IV) represents a compound represented by the aforementioned formula (IV).

In the method of Scheme 4, a compound represented by the formula (III) is allowed to react with compounds represented as $B^1$—X and $B^2$—X, respectively, in the presence of a base and thereby converted into a compound represented by a formula (IV). As the base used, an inorganic base such as sodium hydroxide and potassium hydroxide is preferred when $B^1$ and $B^2$ are alkyl groups, and an organic base such as triethylamine and diisopropylethylamine is preferred when $B^1$ and $B^2$ are alkanoyl groups. Further, in this step, when $B^1$ and $B^2$ are alkanoyl groups, a carboxylic acid anhydride may also be used instead of $B^1$—X and $B^2$—X. Thereafter, a condensation reaction can be performed in the same manner as in Scheme 1 to obtain a target compound represented by the aforementioned formula (I).

When the compound represented by the aforementioned formula (I) contains a polymerizable group, it is preferable to add a polymerization inhibitor to the reaction system as required. Examples of the polymerization inhibitor include nitrobenzene, hydroquinone monomethyl ether and so forth.

The optical retardation plate of the present invention will be explained hereafter.

The 4-membered ring compound represented by the aforementioned formula (I) can be used for producing birefringence mediums in order to reduce the variation in optical properties of the birefringence mediums with wavelength. The conventional birefringence mediums, for example, which is made of rod-like polymerizable liquid crystal compounds that are homogeneously oriented and fixed by polymerization, and is formed by an oriented polymer film, generally has a larger optical phase difference (retardation) for a light of shorter wavelength. On the other hand, the optical retardation plate of the present invention has a larger optical phase difference (retardation) for a light of longer wavelength. When liquid crystal compound is oriented under the presence of the 4-membered compound, the substituents represented as $A^1$-$X^1$— and $A^2$-$X^2$— should be oriented along the perpendicular or pseudo perpendicular direction with respect to a slow axis of the birefringence layer, and thereby wavelength-dependent dispersion of phase difference in the birefringence layer is regulated. More precisely, according to the present invention, the wavelength-dependent dispersion of the phase difference caused by the liquid crystal can be offset by that caused by the substituents of the 4-membered compound represented as $A^1$-$X^1$— and $A^2$-$X^2$— oriented along the perpendicular or pseudo perpendicular direction with respect to a slow axis of birefringence layer. Since the degree of the wavelength-dependent dispersion caused by the latter is larger than that caused by the former, the degree of the offset in shorter wavelength is lager than that in longer wavelength. As a result, it is possible to obtain a wide band optical retardation plate that has a larger phase difference for an incident light of a lager wavelength.

As an embodiment of the optical retardation plate of the present invention, there can be mentioned an optical retardation plate having a support and a birefringence layer provided on the support, wherein the birefringence layer is formed by using a liquid crystal composition containing a liquid crystal compound and a compound represented by the aforementioned formula (I). In this embodiment, the liquid crystal compound is preferably fixed in an oriented state in the birefringence layer. For example, it can be fixed in an oriented state by polymerization using a polymerizable liquid crystal compound. The polymerizable liquid crystal compound used in this embodiment is not particularly limited, and a liquid crystal compound having a polymerizable group (including a crosslinkable group) can be used. However, a rod-like polymerizable liquid crystal compound is preferred. Further, the mixing ratio of the compound represented by the formula (I) and the polymerizable liquid crystal compound in the birefringence layer is determined by refractive index anisotropy and wavelength-dependent dispersion thereof of the polymerizable liquid crystal compound, and usually, it is preferably 0.5–50 weight %, more preferably 1–25 weight %, further preferably 1–15 weight %.

In this embodiment, phase difference to be obtained can be easily controlled to be within a desired range by controlling layer thickness of the birefringence layer.

The optical retardation plate of this embodiment can be produced by a production method comprising a step of applying a composition containing a compound represented by the aforementioned formula (I) and a polymerizable liquid crystal compound on a support, a step of homogeneously orienting the polymerizable liquid crystal compound and a step of fixing the liquid crystal compound in a homogeneously oriented state by polymerization.

The composition may contain auxiliary materials such as a polymerization initiator, polymerization inhibitor, photosensitizer, surface treating agent, liquid crystal orientation aid and crosslinking agent, as required. Although amounts of auxiliary materials added are not particularly limited, it is preferable not to degrade liquid crystal property of a layer to be formed. Mixing ratio of the compound represented by the formula (I) and the polymerizable liquid crystal compound with respect to the total constituents is 50–100 weight %, preferably 65–100 weight %, still more preferably 80–100 weight %.

Although the support is not particularly limited, a glass substrate, polymer film, reflecting plate and so forth can be used. Surface of the support maybe subjected to an orientation treatment as required. Various ordinary methods can be used as the orientation treatment, and a method of providing an oriented liquid crystal layer such as various polyimide type oriented films and polyvinyl alcohol type oriented films on a support and subjecting it to an orientation treatment such as rubbing can be mentioned as a preferred example.

The aforementioned composition can be applied on a support (oriented film, if desired) after dissolved in a solvent or the like. As the application method, there can be used known methods such as curtain coating method, extrusion coating method, roll coating method, spin coating method, dip coating method, bar coating method, spray coating method, slide coating method and printing coating method.

In order to homogeneously orient the liquid crystal compound, it is preferable to apply the composition and then heating the coated layer for ripening. Thereafter, the liquid crystal compound is fixed in a homogenously oriented state by polymerization. Although various known polymerization reactions caused by heat or electromagnetic wave can be used for the polymerization reaction, it is preferable to add a photopolymerization initiator to the composition and cause polymerization as radical polymerization by ultraviolet irradiation.

The optical retardation plate of the present invention is not limited to the configuration of the aforementioned embodiment, and an embodiment of the optical retardation plate (film) consisting only of a birefringence layer obtained by delaminating the birefringence layer formed on a support from the support, an embodiment of the optical retardation plate formed by transferring the birefringence layer to another support, an embodiment of the optical retardation plate comprising a liquid crystal cell (which may be formed by pouring a liquid crystal composition into between a pair of supports), and so forth all fall within the scope of the optical retardation plate of the present invention.

The birefringence of the present invention can be used not only for optical retardation plates and films, but also for various optical elements, which are put in polarization elements, photometric analysis apparatuses, photometric measurement apparatuses, apparatuses for optical experiments and so forth. Further, as for its function, it may be an optical retardation plate (or film) according to any of embodiments for producing linearly polarized light, circularly polarized light or elliptically polarized light. In particular, the birefringence of the present invention can be used for various optical elements, such as optical phase retardation plates and films, elliptically polarizing plates, circularly polarizing plates, polarization rotation plates, polarization conversion prisms, optical pick up devices, reflective liquid crystal devices, semi-transmission type liquid crystal devices, transmission type liquid crystal devices, touch-sensitive panels, antireflection films and displays having films containing the compound of formula(I).

Since the birefringence medium of the present invention can impart a uniform phase difference to an incident light in a certain wavelength region such as a visible light wavelength region, it can be preferably used as an optical retardation plate in which phase difference used for a reflective liquid crystal display is adjusted to $\lambda/4$.

EXAMPLES

Hereafter, the present invention will be more specifically explained with reference to the following examples. However, the scope of the present invention is not limited to the following examples.

Example 1

Synthesis of Compound 1

(1α,2α,3β,4β)-2,4-Bis(4-hydroxyphenyl)-1,3-cyclobutane-dicarboxylic acid (3.28 g) was dissolved in 25 mL of dimethylacetamide and added with 6.9 g of potassium carbonate, 5.48 g of 1-butyl bromide and 600 mg of sodium iodide. After stirred at 100° C. for 5 hours, the mixture was added with water and extracted with hexane. The extract was dried over anhydrous sodium sulfate and then concentrated under reduced pressure. The obtained residue was added with 50 mL of tetrahydrofuran, 50 mL of ethanol and 1 mol/L (1 N) sodium hydroxide aqueous solution and stirred for three days under a reflux condition. The reaction mixture was added with water, washed with hexane and added with hydrochloric acid to obtain precipitates. The obtained precipitates were collected and recrystallized from acetonitrile to obtain 3.22 g of (1α,2α,3β,4β)-2,4-bis(4-butoxyphenyl)-1,3-cyclobutane-dicarboxylic acid.

Then, 440 mg of the (1α,2α,3β,4β)-2,4-bis(4-butoxyphenyl)-1,3-cyclobutane-dicarboxylic acid was dissolved in 10 mL of tetrahydrofuran and added with 260 mg of diisopropylethylamine. The reaction mixture was added dropwise with a solution of 300 mg of isobutyl chloroformate (IBCF) dissolved in 5 mL of tetrahydrofuran under ice cooling, stirred for 20 minutes and added dropwise with a solution of 390 mg of 1-(4-aminophenyl)-2-phenyl-ethyne dissolved in 5 mL of tetrahydrofuran. After stirred for 6 hours, the reaction mixture was added with water and extracted with ethyl acetate, and the extract was dried over anhydrous sodium sulfate and then concentrated under reduced pressure. The obtained residue was purified by silica gel chromatography (eluent: hexane/dichloromethane=1/1 (volume ratio)) to obtain 520 mg of Compound 1.

FAB-MS (M+H)$^+$=791 $^1$H-NMR (CDCl$_3$, δ): 0.94 (t, 6H), 1.35–1.5 (m, 4H), 1.73 (quintet, 4H), 3.87–3.9 (m, 6H), 4.55–4.65 (m, 2H), 6.83 (d, 4H), 6.89 (s, 2H), 7.08 (d, 4H), 7.25–7.4 (m, 14H), 7.4–7.6 (m, 4H)

Example 2

Synthesis of Compound 2

(1α,2α,3β,4β)-2,4-Bis(4-hydroxyphenyl)-1,3-cyclobutane-dicarboxylic acid (9.7 g) was dissolved in 200 mL dimethylformamide, added with 17.9 g of methyl paratoluenesulfonate and stirred at 40° C. for 16 hours. The reaction mixture was added with water, and the obtained solid was taken by filtration to obtain 4.6 g of dimethyl (1α,2α,3β,4β)-2,4-bis(4-hydroxyphenyl)-1,3-cyclobutane-dicarboxylate. The dimethyl (1α,2α,3β,4β)-2,4-bis(4-hydroxyphenyl)-1,3-cyclobutane-dicarboxylate (710 mg) was dissolved in 15 mL of the mixture of dimethylformamide and tetrahydrofuran, added with 600 mg of sodium iodide, 1.38 g of potassium carbonate and 770 mg of 1-octyl bromide and stirred at 80° C. for 7 hours. The reaction mixture was added to water and extracted with ethyl acetate. The organic layer was washed with water, then dried over sodium sulfate and concentrated under reduced pressure. Then, the residue was purified by silica gel chromatography to obtain 400 mg of dimethyl (1α,2α,3β,4β)-2,4-bis(4-octyloxyphenyl)-1,3-cyclobutane-dicarboxylate.

The dimethyl (1α,2α,3β,4β)-2,4-bis(4-octyloxyphenyl)-1,3-cyclobutane-dicarboxylate (380 mg) was dissolved in 10 mL of tetrahydrofuran, added with 10 mL of 1 mol/L (1 N) sodium hydroxide aqueous solution and 10 mL of ethanol and stirred for one and half days under a reflux condition. The reaction mixture was washed with ethyl acetate and acidified with addition of hydrochloric acid, and the obtained precipitates were taken by filtration to obtain 280 mg of (1α,2α,3β,4β)-2,4-bis(4-octyloxyphenyl)-1,3-cyclobutane-dicarboxylic acid. The (1α,2α,3β,4β)-2,4-bis(4-octyloxyphenyl)-1,3-cyclobutane-dicarboxylic acid (900 mg) was dissolved in 15 mL of tetrahydrofuran, added with 0.43 g of diisopropylethylamine and then added dropwise with a solution of 450 mg of IBCF dissolved in 5 mL of tetrahydrofuran at −15° C. After stirred for 20 minutes, the reaction mixture was added dropwise with 640 mg of 1-(4-aminophenyl)-2-phenyl-ethyne dissolved in 5 mL of tetrahydrofuran. After stirred for 6 hours, the reaction mixture was added with water and extracted with ethyl acetate, and the extract was dried over anhydrous sodium sulfate and then concentrated under reduced pressure. The obtained residue was purified by silica gel chromatography (eluent: hexane/dichloromethane=1/1) to obtain 310 mg of Compound 2.

FAB-MS $(M+H)^+$=903 $^1$H-NMR (CDCl$_3$, δ): 0.87 (t, 6H), 1.2–1.5 (m, 20H), 1.73 (quintet, 4H), 3.8–3.9 (m, 6H), 4.6–4.7 (m, 2H), 6.82 (s, 2H), 6.83 (d, 4H), 7.09 (d, 4H), 7.25–7.4 (m, 14H), 7.4–7.6 (m, 4H)

Example 3

Synthesis of Compound 3

Compound 3 was synthesized according to the method of Example 2 except that the 1-octyl bromide used in Example 2 was replaced with 1-dodecyl bromide.

FAB-MS $(M+H)^+$=1015 $^1$H-NMR (CDCl$_3$, δ): 0.88 (t, 6H), 1.2–1.5 (m, 36H), 1.73 (quintet, 4H), 3.8–3.9 (m, 6H), 4.6–4.7 (m, 2H), 6.78 (s, 2H), 6.84 (d, 4H), 7.10 (d, 4H), 7.2–7.4 (m, 14H), 7.5–7.6 (m, 4H)

Example 4

Synthesis of Compound 4

Compound 4 was synthesized according to the method of Example 2 except that the 1-octyl bromide used in Example 2 was replaced with 1-stearyl bromide.

FAB-MS $(M+H)^+$=1183 $^1$H-NMR (CDCl$_3$, δ): 0.88 (t, 6H), 1.2–1.5 (m, 60H), 1.73 (quintet, 4H), 3.8–3.9 (m, 6H), 4.6–4.7 (m, 2H), 6.78 (s, 2H), 6.84 (d, 4H), 7.10 (d, 4H), 7.2–7.4 (m, 14H), 7.5–7.6 (m, 4H)

Example 5

Synthesis of Compound 5

Compound 5 was synthesized according to the method of Example 2 except that the 1-(4-aminophenyl)-2-phenyl-ethyne used in Example 2 was replaced with 4-aminobiphenyl.

FAB-MS $(M+H)^+$=855

Example 6

Synthesis of Compound 6

Compound 6 was synthesized according to the method of Example 2 except that the 1-(4-aminophenyl)-2-phenyl-ethyne used in Example 2 was replaced with 1-(4-aminophenyl)-2-phenyl-buta-1,3-diyne and the 1-octyl bromide used in Example 2 was replaced with 1-dodecyl bromide.

FAB-MS $(M+H)^+$=1063

Example 7

Synthesis of Compound 7

Compound 7 was synthesized according to the method of Example 2 except that the 1-(4-aminophenyl)-2-phenyl-ethyne used in Example 2 was replaced with phenyl 4-aminobenzoate.

FAB-MS $(M+H)^+$=943

Example 8

Synthesis of Compound 8

Compound 8 was synthesized according to the method of Example 2 except that the 1-(4-aminophenyl)-2-phenyl-ethyne used in Example 2 was replaced with 4-aminophenyl benzoate.

FAB-MS $(M+H)^+$=943

Example 9

Synthesis of Compound 9

Compound 9 was synthesized according to the method of Example 2 except that the 1-(4-aminophenyl)-2-phenyl-ethyne used in Example 2 was replaced with 4-aminophenyl 2-thiophenecarboxylate.

FAB-MS $(M+H)^+$=955

Example 10

Synthesis of Compound 10

Compound 10 was synthesized according to the method of Example 2 except that the 1-(4-aminophenyl)-2-phenyl-ethyne used in Example 2 was replaced with 1-(4-aminophenyl)-2-thienyl-ethyne.

FAB-MS $(M+H)^+$=915

Example 11

Synthesis of Compound 11

Compound 11 was synthesized according to the method of Example 4 except that the 1-(4-aminophenyl)-2-phenyl-ethyne used in Example 4 was replaced with biphenyl 4-aminobenzoate.

FAB-MS $(M+H)^+$=1375

Example 12

Synthesis of Compound 12

Compound 12 was synthesized according to the method of Example 2 except that the 1-(4-aminophenyl)-2-phenyl-ethyne used in Example 2 was replaced with 4-aminophenyl 4-methylthiobenzoate.

FAB-MS $(M+H)^+$=1035

Example 13

Synthesis of Compound 13

Compound 13 was synthesized according to the method of Example 2 except that the 1-(4-aminophenyl)-2-phenyl-ethyne used in Example 2 was replaced with 4-phenylthiophenol.

FAB-MS $(M+H)^+$=889

Example 14

Synthesis of Compound 14

Compound 14 was synthesized according to the method of Example 2 except that the 1-(4-aminophenyl)-2-phenyl-ethyne used in Example 2 was replaced with 4-hydroxybiphenyl.

FAB-MS $(M+H)^+$=857

Example 15

Synthesis of Compound 15

Compound 15 was synthesized according to the method of Example 2 except that the 1-(4-aminophenyl)-2-phenyl-

Example 16

Synthesis of Compound 16

Compound 16 was synthesized according to the method of Example 2 except that the 1-(4-aminophenyl)-2-phenyl-ethyne used in Example 2 was replaced with 4-aminobenzoic acid phenylamide.

FAB-MS (M+H)$^+$=941

Example 17

Synthesis of Compound 17

Compound 17 was synthesized according to the method of Example 2 except that the 1-(4-aminophenyl)-2-phenyl-ethyne used in Example 2 was replaced with 4-aminobenzoic acid 4-methoxyphenylthioester.

FAB-MS (M+H)$^+$=1035

Example 18

Synthesis of Compound 18

Compound 18 was synthesized according to the method of Example 2 except that the 1-(4-aminophenyl)-2-phenyl-ethyne used in Example 2 was replaced with 4-hydroxystilbene.

FAB-MS (M+H)$^+$=909

Example 19

Synthesis of Compound 19

Compound 19 was synthesized according to the method of Example 2 except that the 1-(4-aminophenyl)-2-phenyl-ethyne was replaced with 4-aminobenzoic acid 4-methylphenylthioester.

FAB-MS (M+H)$^+$=1003

Example 20

Synthesis of Compound 20

(1α,2α,3β,4β)-2,4-Bis(4-hydroxyphenyl)-1,3-cyclobutane-dicarboxylic acid (3.28 g) was dissolved in 25 mL of dimethylacetamide and added dropwise with a solution of 2.1 g of triethylamine and 3.54 g of nonanoyl chloride in dimethylacetamide (10 mL). After stirred at room temperature for 5 hours, the reaction mixture was added with water, acidified with hydrochloric acid and extracted with ethyl acetate. The extract was dried over anhydrous sodium sulfate and concentrated under reduced pressure, and the residue was recrystallized from acetonitrile to obtain 2.15 g of (1α,2α,3β,4β)-2,4-bis(4-nonanoyloxyphenyl)-1,3-cyclobutane-dicarboxylic acid. Then, 610 mg of the (1α,2α,3β,4β)-2,4-bis(4-nonanoyloxyphenyl)-1,3-cyclobutane-dicarboxylic acid was dissolved in 10 mL of tetrahydrofuran and added with 260 mg of diisopropylethylamine. The reaction mixture was added dropwise with a solution of 300 mg of isobutyl chloroformate (IBCF) dissolved in 5 mL of tetrahydrofuran under ice cooling, stirred for 20 minutes and added dropwise with a solution of 390 mg of 1-(4-aminophenyl)-2-phenyl-ethyne dissolved in 5 mL of tetrahydrofuran. After stirred for 6 hours, the reaction mixture was added with water and extracted with ethyl acetate, and the extract was dried over anhydrous sodium sulfate and then concentrated under reduced pressure. The obtained residue was recrystallized from a mixture of ethyl acetate and acetonitrile to obtain 410 mg of Compound 20.

FAB-MS (M+H)$^+$=959

Example 21

Synthesis of Compound 21

Compound 21 was synthesized according to the method of Example 20 except that the (1α,2α,3β,4β)-2,4-bis(4-hydroxyphenyl)-1,3-cyclobutane-dicarboxylic acid used in Example 20 was replaced with (1α,2α,3β,4β)-2,4-bis(4-aminophenyl)-1,3-cyclobutane-dicarboxylic acid.

FAB-MS (M+H)$^+$=957

Example 22

Synthesis of Compound 22

(1α,2α,3β,4β)-2,4-bis(4-hydroxyphenyl)-1,3-cyclobutane-dicarboxylic acid (3.28 g) was dissolved in 25 mL of dimethylacetamide, added with 2.1 g of triethylamine and added dropwise with a solution of 2.1 g of acetic anhydride in dimethylacetamide (10 mL). After stirred at room temperature for 8 hours, the reaction mixture was added with water, acidified with hydrochloric acid and extracted with ethyl acetate. The extract was dried over anhydrous sodium sulfate and then concentrated under reduced pressure to obtain 1.86 g of (1α,2α,3β,4β)-2,4-bis(4-acetyloxyphenyl)-1,3-cyclobutane-dicarboxylic acid. Then, 410 mg of the (1α,2α,3β,4β)-2,4-bis(4-acetyloxyphenyl)-1,3-cyclobutane-dicarboxylic acid was dissolved in 10 mL of tetrahydrofuran and added with 260 mg of diisopropylethylamine. The reaction mixture was added dropwise with a solution of 300 mg of isobutyl chloroformate (IBCF) dissolved in 5 mL of tetrahydrofuran under ice cooling, stirred for 20 minutes and then added dropwise with a solution of 390 mg of 1-(4-aminophenyl)-2-phenyl-ethyne dissolved in 5 mL of tetrahydrofuran. After stirred for 6 hours, the reaction mixture was added with water and extracted with ethyl acetate, and the extract was dried over anhydrous sodium sulfate and then concentrated under reduced pressure. The obtained residue was recrystallized from a mixture of ethyl acetate and acetonitrile to obtain 390 mg of (1α,2α,3β,4β)-2,4-bis(4-acetyloxyphenyl)-1,3-cyclobutane-dicarboxylic acid di-1-(4-aminophenyl)-2-phenyl-ethynamide.

In an amount of 390 mg of the obtained (1α,2α,3β,4β)-2,4-bis(4-acetyloxyphenyl)-1,3-cyclobutane-dicarboxylic acid di-1-(4-aminophenyl)-2-phenyl-ethynamide was dissolved in 50 mL of tetrahydrofuran and added with 50 mL of ethanol and 1 mol/L (1 N) sodium hydroxide aqueous solution. After stirred for 3 hours under a reflux condition, the reaction mixture was added with water and extracted with ethyl acetate. The extract was dried over anhydrous sodium sulfate and concentrated under reduced pressure. The obtained residue was dissolved in 20 mL of dimethylacetamide, added with 250 mg of potassium carbonate, 30 mg of sodium iodide and 0.2 mL of nitrobenzene, then added dropwise with a solution of 261 mg of 8-chlorooctyl acrylate dissolved in 5 mL of dimethylacetamide and stirred at 100° C. for 6 hours. The reaction mixture was added with water and extracted with ethyl acetate. The extract was dried over anhydrous sodium sulfate and concentrated under reduced pressure. The obtained residue was purified by silica gel chromatography (eluent: chloroform) to obtain 170 mg of Compound 22.

FAB-MS (M+H)$^+$=1043 $^1$H-NMR (DMSO-d$_6$, δ): 1.2–1.5 (m, 16H), 1.7–1.8 (m, 8H), 3.92 (t, 4H), 3.96–4.02 (m, 2H), 4.12 (t, 4H), 4.4–4.5 (m, 2H), 5.94 (m, 2H), 6.18 (m, 2H), 6.34 (m, 2H), 6.83 (d, 4H), 7.28 (d, 4H), 7.4–7.6 (m, 18H), 10.06 (s, 2H)

Example 23

Synthesis of Compound 23

Compound 23 was synthesized according to the method of Example 22 except that the 8-chlorooctyl acrylate used in Example 22 was replaced with 8-chlorooctyl methacrylate.

FAB-MS (M+H)$^+$=1071

Example 24

Synthesis of Compound 24

Compound 24 was synthesized according to the method of Example 22 except that the 8-chlorooctyl acrylate used in Example 22 was replaced with 4-chlorobutyl propionate.

FAB-MS (M+H)$^+$=935

Example 25

Synthesis of Compound 25

Compound 25 was synthesized according to the method of Example 22 except that the 8-chlorooctyl acrylate used in Example 22 was replaced with propionic acid 8-chlorobutylamide.

FAB-MS (M+H)$^+$=933

Example 26

Synthesis of Compound 26

Compound 26 was synthesized according to the method of Example 20 except that the nonanoyl chloride used in Example 20 was replaced with trans-3-hexenoyl chloride.

FAB-MS (M+H)$^+$=871

Example 27

Synthesis of Compound 27

Compound 27 was synthesized according to the method of Example 20 except that the nonanoyl chloride used in Example 20 was replaced with trans-4-pentyl-cyclohexanoyl chloride.

FAB-MS (M+H)$^+$=1039

Example 28

Synthesis of Compound 28

Compound 28 was synthesized according to the method of Example 2 except that the 1-(4-aminophenyl)-2-phenyl-ethyne used in Example 2 was replaced with 4-hydroxybiphenyl 4-phenylbenzoate.

TOF-MS (M+H)$^+$=1250

Example 29

Synthesis of Compound 29

Compound 29 was synthesized according to the method of Example 22 except that the 8-chlorooctyl acrylate used in Example 22 was replaced with 4-chlorobutyl acetate.

FAB-MS (M+H)$^+$=907 $^1$H-NMR (DMSO-d$_6$, δ): 1.7–1.8 (m, 8H), 1.97 (s, 6H), 3.8–3.9 (m, 6H), 4.10 (t, 4H), 4.35–4.5 (m, 2H), 6.84 (d, 4H), 7.28 (d, 4H), 7.4–7.6 (m, 18H), 10.05 (s, 2H)

Example 30

Synthesis of Compound 30

Compound 30 was synthesized according to the method of Example 22 except that the 8-chlorooctyl acrylate used in Example 22 was replaced with 4-chlorobutyl acrylate.

FAB-MS (M+H)$^+$=931 $^1$H-NMR (DMSO-d$_6$, δ): 1.7–1.8 (m, 8H), 3.92 (t, 4H), 3.96–4.02 (m, 2H), 4.12 (t, 4H), 4.4–4.5 (m, 2H), 5.94 (m, 2H), 6.18 (m, 2H), 6.34 (m, 2H), 6.83 (d, 4H), 7.28 (d, 4H), 7.4–7.6 (m, 18H), 10.06 (s, 2H)

Example 31

Synthesis of Compound 31

Compound 31 was synthesized according to the method of Example 2 except that the (1α,2α,3β,4β)-2,4-bis(4-hydroxyphenyl)-1,3-cyclobutane-dicarboxylic acid used in Example 2 was replaced with (1α,2α,3β,4β)-2,4-bis(3-methoxy-4-hydroxyphenyl)-1,3-cyclobutane-dicarboxylic acid.

FAB-MS (M+H)$^+$=963

Example 32

Synthesis of Compound 32

Compound 32 was synthesized according to the method of Example 2 except that the 1-(4-aminophenyl)-2-phenyl-ethyne used in Example 2 was replaced with 1-(4-aminophenyl)-2-(4-hexyloxyphenyl)-ethyne.

FAB-MS (M+H)$^+$=1215

Example 33

Synthesis of Compound 33

Compound 33 was synthesized according to the method of Example 20 except that the nonanoyl chloride used in Example 20 was replaced with 4-heptyle-benzoate chloride.

FAB-MS (M+H)$^+$=1083

Example 34

Synthesis of Compound 34

Compound 34 was synthesized according to the method of Example 20 except that the nonanoyl chloride used in Example 20 was replaced with 4-(4-acryloyloxybutyloxy)-benzoate chloride.

FAB-MS (M+H)$^+$=1083

Example 35

Production of Optical Retardation Plate

A coating solution having the composition mentioned below was coated by spin coating (1000 rpm) on a polyimide type alignment layer (SE-150, Nissan Chemical Industries), which was coated on a glass substrate and subjected to rubbing treatment, then successively dried, heated (ripening of orientation) and irradiated with an ultraviolet ray at 90° C. to produce an optical retardation plate.

| <<Composition of coating solution for liquid crystal layer>> | |
|---|---|
| Compound 22 | 2.0 weight % |
| Rod-like polymerizable liquid crystal compound mentioned below | 20.0 weight % |
| Fluorine-containing surface treating agent | 0.3 weight % |
| Photopolymerization initiator (Irgacure 907, Ciba Geigy) | 3.0 weight % |
| Phenothiazine | 1.0 weight % |
| Methyl ethyl ketone | 73.7 weight % |

Rod-like polymerizable liquid crystal compound

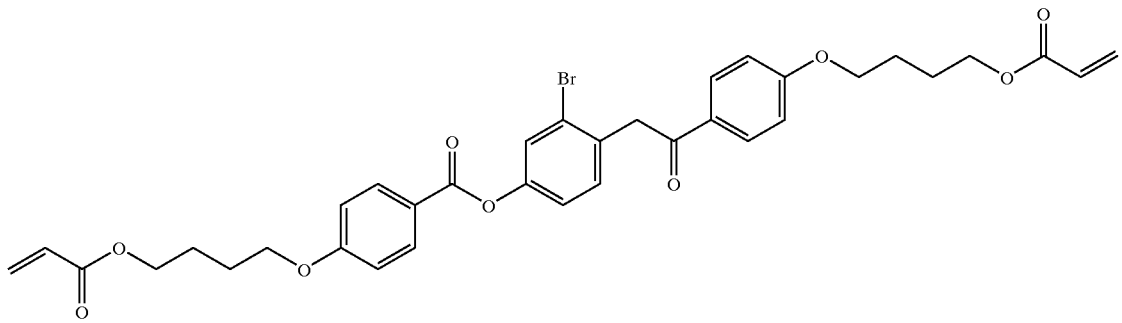

Example 36

Production of Optical Retardation Plate

An optical retardation plate was produced in the same manner as in Example 35 by using a coating solution having the following composition.

| <<Composition of coating solution for liquid crystal layer>> | |
|---|---|
| Compound 22 | 2.0 weight % |
| Rod-like polymerizable liquid crystal compound mentioned below | 20.0 weight % |
| Fluorine-containing surface treating agent | 0.3 weight % |
| Photopolymerization initiator (Irgacure 907, Ciba Geigy) | 3.0 weight % |
| Phenothiazine | 1.0 weight % |
| Methyl ethyl ketone | 73.7 weight % |

Rod-like polymerizable liquid crystal compound

Example 37

Production of Optical Retardation Plate

An optical retardation plate was produced in the same manner as in Example 35 by using a coating solution having the following composition.

| <<Composition of coating solution for liquid crystal layer>> | |
|---|---|
| Compound 2 | 2.0 weight % |
| Rod-like polymerizable liquid crystal compound mentioned below | 20.0 weight % |
| Crosslinking agent (Biscoat 360, Osaka Organic Chemical Industry) | 3.0 weight % |
| Fluorine-containing surface treating agent | 0.3 weight % |
| Photopolymerization initiator (Irgacure 907, Ciba Geigy) | 3.0 weight % |
| Phenothiazine | 1.0 weight % |
| Methyl ethyl ketone | 70.7 weight % |

Rod-like polymerizable liquid crystal compound

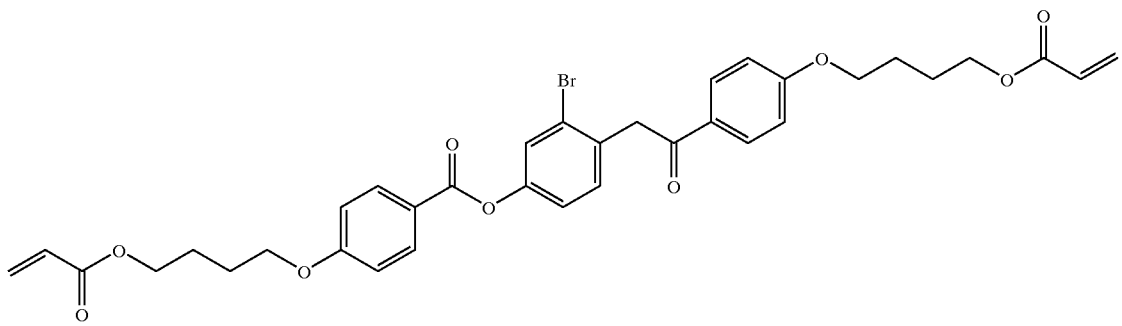

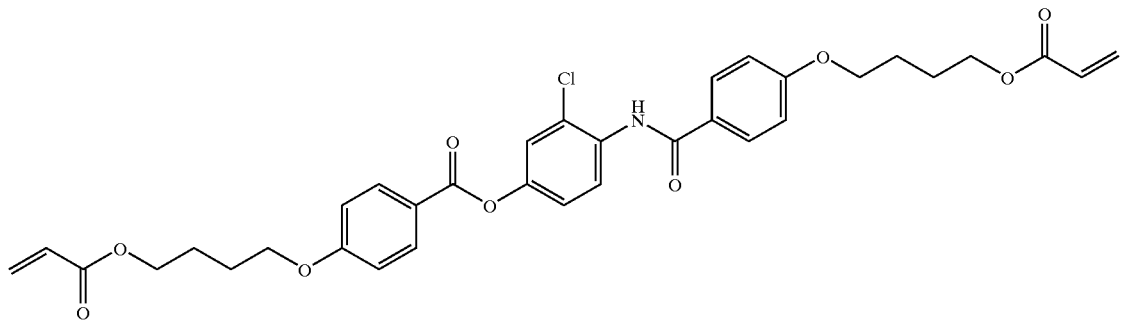

Example 38

Measurement of Optical Phase Difference

Figure 2:
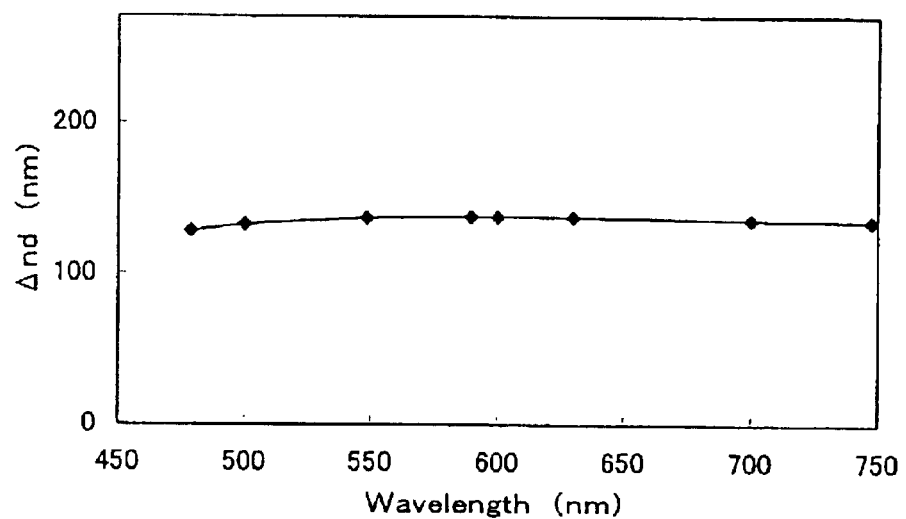
FIG. 2 shows a plot representing wavelength dependency of optical phase difference in a visible region for the optical retardation plate produced in Example 33.
Figure 3:
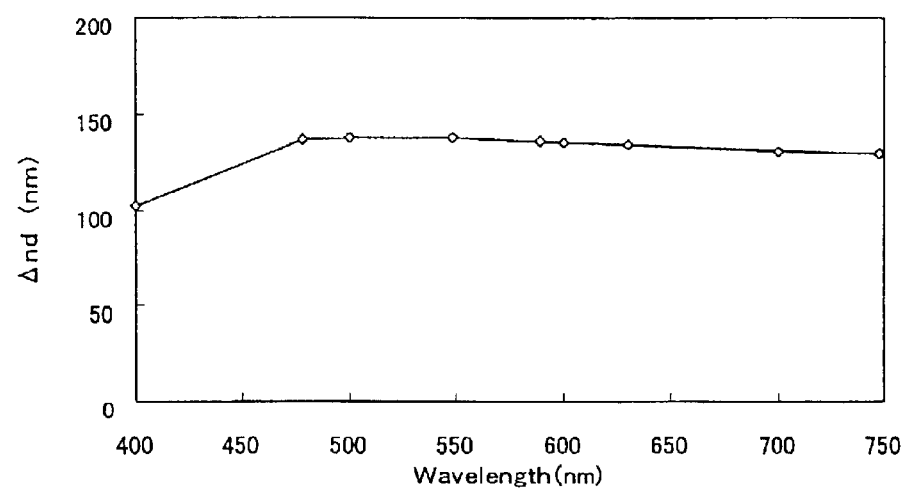
FIG. 3 shows a plot representing wavelength dependency of optical phase difference in a visible region for the optical retardation plate produced in Example 34.

Optical phase differences in the wavelength range of 450–750 nm of the optical retardation plates obtained in Examples 35 to 37 were measured by using KOBRA produced by Oji Scientific Instruments. A plot representing wavelength dependency of optical phase difference in the aforementioned wavelength region (visible region) for the optical retardation plate of Example 35 is shown in FIG. 1, a plot representing wavelength dependency of optical phase difference in the aforementioned wavelength region (visible region) for the optical retardation plate of Example 36 is shown in FIG. 2, and a plot representing wavelength dependency of optical phase difference in the aforementioned wavelength region (visible region) for the optical retardation plate of Example 37 is shown in FIG. 3. As seen from these results, all the optical retardation plates showed favorable phase difference as λ/4 for a wide band.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A 4-membered ring compound represented by the following formula (I):

Formula (I)

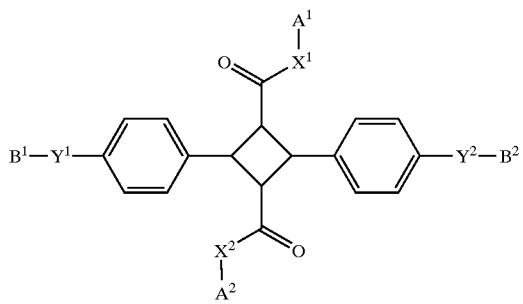

(in the formula, $X^1$ and $X^2$ each independently represent an oxygen atom, a sulfur atom or a substituted or unsubstituted imino group, $Y^1$ and $Y^2$ each independently represent a single bond, an oxygen atom or a substituted or unsubstituted imino group, $B^1$ and $B^2$ each independently represent an optionally substituted aliphatic group, aliphatic carbonyl group, aromatic group or aromatic carbonyl group, having 1–20 carbon atoms, two of the benzene rings directly bonding to the cyclobutane ring each may have a substituent on the rings, and $A^1$ and $A^2$ each independently represent a group represented by the following formula (II):

Formula (II)

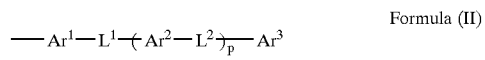

(in the formula, $Ar^1$, $Ar^2$ and $Ar^3$ each independently represent a cyclic group having 5–14 carbon atoms, which may have a substituent on the ring, $L^1$ and $L^2$ each independently represent a single bond or a divalent linking group, p represents an integer of 0–2, and when p is 2, two of $Ar^2$ and two of $L^2$ may be identical to or different from each other)).

2. The compound of claim 1, wherein rings of the cyclic groups represented by $Ar^1$, $Ar^2$ and $Ar^3$ are rings selected from a benzene ring, a thiophene ring and a naphthalene ring.

3. The compound of claim 1, wherein $L^1$ and $L^2$ each independently represent a single bond or a divalent linking group selected from an acetylene, a bisacetylene, a carbonyloxy and an oxycarbonyl.

4. The compound of claim 1, wherein $L^1$ and $L^2$ each independently represent an acetylene or a bisacetylene.

5. The compound of claim 1, wherein $Y^1$ and $Y^2$ each independently represent an oxygen atom or a substituted or unsubstituted imino group.

6. The compound of claim 1, wherein $B^1$ and $B^2$ each independently represent an aliphatic group or aliphatic carbonyl group substituted with a substituent containing a divalent group consisting of an oxygen atom, a sulfur atom, a carbonyl, a substituted or unsubstituted imino group or a combination thereof.

7. The compound of claim 1, wherein $B^1$ and $B^2$ each independently represent an aliphatic group or aliphatic carbonyl group substituted with a substituent containing a polymerizable group.

8. The compound of claim 1, wherein $B^1$ and $B^2$ each independently represent an aliphatic group or aliphatic carbonyl group substituted with an acryloyl group or a methacryloyl group.

9. A birefringence medium containing a compound according to claim 1.

10. The birefringence medium of claim 9, further comprising at least one kind of liquid crystal compound fixed in an oriented state.

11. The birefringence medium of claim 9, wherein the content of the 4-membered compound is 0.5 to 50 weight %.

12. An optical element comprising a birefringence medium containing a compound according to claim 1.

13. The optical element of claim 12, wherein the birefringence medium comprises at least one kind of liquid crystal compound fixed in an oriented state.

14. The optical element of claim 12, wherein the content of the 4-membered compound is 0.5 to 50 weight % in the birefringence medium.

* * * * *